US007645613B2

(12) United States Patent
Ivey et al.

(10) Patent No.: US 7,645,613 B2
(45) Date of Patent: *Jan. 12, 2010

(54) MASS SPECTROMETRY TECHNIQUES FOR DETERMINING THE STATUS OF SEPSIS IN AN INDIVIDUAL

(75) Inventors: Richard M. Ivey, Parkton, MD (US); Thomas M. Gentle, Jr., Red Lion, PA (US); Richard L. Moore, Glenville, PA (US); Michael L. Towns, Timonium, MD (US); Gary Siuzdak, San Diego, CA (US); Elizabeth J. Want, San Diego, CA (US); Zhouxin Shen, San Diego, CA (US); Nicholas Bachur, Jr., Monkton, MD (US); Robert W. Rosenstein, Ellicott City, MD (US); James G. Nadeau, Ellicott City, MD (US); Paul E. Goldenbaum, Hampstead, MD (US); Song Shi, Reisterstown, MD (US); Donald Copertino, Catonsville, MD (US); James Garrett, Baltimore, MD (US); Gregory Tice, Lutherville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 588 days.

This patent is subject to a terminal disclaimer.

(21) Appl. No.: 11/647,688

(22) Filed: Dec. 28, 2006

(65) Prior Publication Data

US 2007/0184512 A1 Aug. 9, 2007

Related U.S. Application Data

(63) Continuation of application No. 10/704,758, filed on Nov. 12, 2003, now abandoned.

(60) Provisional application No. 60/425,322, filed on Nov. 12, 2002, provisional application No. 60/503,548, filed on Sep. 17, 2003.

(51) Int. Cl.
    *G01N 24/00* (2006.01)
(52) U.S. Cl. .......................... 436/173; 436/89
(58) Field of Classification Search .................. None
    See application file for complete search history.

(56) References Cited

U.S. PATENT DOCUMENTS 4,198,389 A 4/1980 Wadsworth
(Continued)

FOREIGN PATENT DOCUMENTS

EP 1 355 158 A1 10/2003
(Continued)

OTHER PUBLICATIONS

Anthony et al., 2000, "Rapid diagnosis of bacteremia by universal amplification 23S ribosomal DNA followed by hybridization to an oligonucleotide array," J. Clin. Microbiol. 38(2): 781-88.
(Continued)

*Primary Examiner*—Yelena G Gakh
(74) *Attorney, Agent, or Firm*—Jones Day

(57) ABSTRACT

Mass spectrometry techniques for determining the status of sepsis in an individual are provided. A biomarker profile resolved from a biological sample, taken from the individual, using a mass spectrometry technique is compared to a reference biomarker profile. A single such comparison classifies the individual as belonging to or not belonging to a reference population. The individual's biomarker profile and the reference biomarker profile comprise a plurality of ions each having a mass-to-charge ratio of about 100 Daltons to about 1000 Daltons. The plurality of ions can be detected by electrospray ionization mass spectrometry in positive mode. The comparison uses a decision rule, such as a classification tree, that determines the status of sepsis in the individual without requiring knowledge of the identity of the biomarkers in the biomarker profile from the individual and without requiring knowledge of the identity of the biomarkers in the reference biomarker profile.

25 Claims, 11 Drawing Sheets

U.S. PATENT DOCUMENTS

| | | |
|---|---|---|
| 4,329,152 A | 5/1982 | Lauwerys et al. |
| 4,721,730 A | 1/1988 | Furuyoshi et al. |
| 4,770,774 A | 9/1988 | Ida et al. |
| 4,872,983 A | 10/1989 | Dimantoglou et al. |
| 4,952,323 A | 8/1990 | Nakabayashi et al. |
| 5,051,185 A | 9/1991 | Watanabe et al. |
| 5,051,371 A | 9/1991 | Nissen et al. |
| 5,093,271 A | 3/1992 | Yamamoto |
| 5,175,113 A | 12/1992 | Nissen et al. |
| 5,272,258 A | 12/1993 | Siegel et al. |
| 5,358,852 A | 10/1994 | Wu |
| 5,426,181 A | 6/1995 | Lee et al. |
| 5,484,705 A | 1/1996 | White et al. |
| 5,500,345 A | 3/1996 | Soe et al. |
| 5,639,617 A | 6/1997 | Bohuon |
| 5,646,005 A | 7/1997 | Kudsk |
| 5,780,237 A | 7/1998 | Bursten et al. |
| 5,804,367 A | 9/1998 | White et al. |
| 5,804,370 A | 9/1998 | Romaschin et al. |
| 5,830,679 A | 11/1998 | Bianchi et al. |
| 5,882,872 A | 3/1999 | Kudsk |
| 5,904,663 A | 5/1999 | Braverman et al. |
| 5,981,180 A | 11/1999 | Chandler et al. |
| 6,077,665 A | 6/2000 | Weirich et al. |
| 6,190,872 B1 | 2/2001 | Slotman |
| 6,251,598 B1 | 6/2001 | di Giovine et al. |
| 6,268,222 B1 | 7/2001 | Chandler et al. |
| 6,303,321 B1 | 10/2001 | Tracey et al. |
| 6,406,862 B1 | 6/2002 | Krakauer |
| 6,416,487 B1 | 7/2002 | Braverman et al. |
| 6,420,526 B1 | 7/2002 | Ruben et al. |
| 6,534,648 B1 | 3/2003 | Pardy et al. |
| 6,548,646 B1 | 4/2003 | Ebrahim et al. |
| 6,579,719 B1 | 6/2003 | Hutchens et al. |
| 6,592,822 B1 | 7/2003 | Chandler |
| 6,599,331 B2 | 7/2003 | Chandler et al. |
| 6,675,104 B2 | 1/2004 | Paulse et al. |
| 6,682,741 B1 | 1/2004 | Ribaudo et al. |
| 6,692,916 B2 | 2/2004 | Bevilacqua et al. |
| 6,756,483 B1 | 6/2004 | Bergmann et al. |
| 6,838,250 B2 | 1/2005 | Scalice et al. |
| 6,872,541 B2 | 3/2005 | Mills |
| 6,930,085 B2 | 8/2005 | Fogelman et al. |
| 2002/0019704 A1 | 2/2002 | Tusher et al. |
| 2002/0150534 A1 | 10/2002 | Yu et al. |
| 2003/0004402 A1 | 1/2003 | Hitt et al. |
| 2003/0027176 A1 | 2/2003 | Dailey |
| 2003/0049851 A1 | 3/2003 | Toh et al. |
| 2003/0057106 A1 | 3/2003 | Shen et al. |
| 2003/0100122 A1 | 5/2003 | Heinecke |
| 2003/0194752 A1 | 10/2003 | Anderson et al. |
| 2003/0219771 A1 | 11/2003 | Bevilacqua et al. |
| 2003/0228625 A1 | 12/2003 | Toh et al. |
| 2004/0009503 A1 | 1/2004 | Fu et al. |
| 2004/0038201 A1 | 2/2004 | Nau et al. |
| 2004/0072237 A1 | 4/2004 | Schweitzer |
| 2004/0096917 A1 | 5/2004 | Ivey et al. |
| 2004/0097460 A1 | 5/2004 | Ivey et al. |
| 2004/0106142 A1 | 6/2004 | Ivey et al. |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0133352 A1 | 7/2004 | Bevilacqua et al. |
| 2004/0157242 A1 | 8/2004 | Ivey et al. |
| 2004/0175754 A1 | 9/2004 | Bar-Or et al. |
| 2004/0180396 A1 | 9/2004 | Bergmann et al. |
| 2004/0219568 A1 | 11/2004 | Bevilacqua et al. |
| 2004/0225447 A1 | 11/2004 | Bevilacqua et al. |
| 2004/0225449 A1 | 11/2004 | Bevilacqua et al. |
| 2004/0336557 | 11/2004 | Bevilacqua et al. |
| 2004/0253637 A1 | 12/2004 | Buechler et al. |
| 2004/0259090 A1 | 12/2004 | Zipel et al. |
| 2005/0009074 A1 | 1/2005 | Thompson |
| 2005/0037344 A1 | 2/2005 | Stuhlmuller et al. |
| 2005/0059104 A1 | 3/2005 | Bergmann |
| 2005/0060101 A1 | 3/2005 | Bevilacqua et al. |
| 2005/0064506 A1 | 3/2005 | Bergmann |
| 2005/0069958 A1 | 3/2005 | Mills et al. |
| 2005/0074811 A1 | 4/2005 | Bergmann |
| 2005/0079490 A1 | 4/2005 | Stuber et al. |
| 2005/0106645 A1 | 5/2005 | Bergmann |
| 2005/0130242 A1 | 6/2005 | Bergmann et al. |
| 2005/0148029 A1 | 7/2005 | Buechler et al. |
| 2005/0164238 A1 | 7/2005 | Valkirs et al. |
| 2005/0239150 A1 | 10/2005 | Bergmann |

FOREIGN PATENT DOCUMENTS

| | | |
|---|---|---|
| EP | 1 369 693 A1 | 12/2003 |
| RU | RU 2072103 | 8/1997 |
| SU | SU 1504597 | 9/1993 |
| WO | WO 92/21364 | 12/1992 |
| WO | WO 94/28418 | 12/1994 |
| WO | WO 95/20163 | 7/1995 |
| WO | WO 96/41291 | 12/1996 |
| WO | WO 98/01738 | 1/1998 |
| WO | WO 00/42222 | 7/2000 |
| WO | WO 00/46603 | 8/2000 |
| WO | WO 01/04630 | 1/2001 |
| WO | WO 01/63280 | 8/2001 |
| WO | WO 01/96864 A2 | 12/2001 |
| WO | WO 02/42733 A2 | 5/2002 |
| WO | WO 02/058721 | 8/2002 |
| WO | WO 02/08747 A2 | 11/2002 |
| WO | WO 02/088744 | 11/2002 |
| WO | WO 03/040404 A1 | 5/2003 |
| WO | WO 03/048776 A1 | 6/2003 |
| WO | WO 03/048777 A1 | 6/2003 |
| WO | WO 03/048778 A1 | 6/2003 |
| WO | WO 03/048782 A1 | 6/2003 |
| WO | WO 03/073099 A1 | 9/2003 |
| WO | 1 355 159 A1 | 10/2003 |
| WO | WO 03/084388 | 10/2003 |
| WO | WO 2004/005539 A1 | 1/2004 |
| WO | WO 2004/043223 | 5/2004 |
| WO | WO 2004/044554 A2 | 5/2004 |
| WO | WO 2004/044555 A2 | 5/2004 |
| WO | WO 2004/044556 A2 | 5/2004 |
| WO | WO 2004/053148 A1 | 6/2004 |
| WO | WO 2004/053155 A1 | 6/2004 |
| WO | WO 2004/053457 A2 | 6/2004 |
| WO | WO 2004/057034 | 7/2004 |
| WO | WO 2004/059293 A2 | 7/2004 |
| WO | WO 2004/087949 A2 | 10/2004 |
| WO | WO 2004/108957 A2 | 12/2004 |
| WO | WO 2005/033327 A2 | 4/2005 |
| WO | WO 2005/064307 A2 | 7/2005 |

OTHER PUBLICATIONS

Ambroise et al., 2002, "Selection bias in gene extraction on the basis of microarray gene-expression data," Proc. Nat'l Acad. Sci. USA 99(10): 6562-66.

Angus et al., 2001, "Epidemiology of severe sepsis in the United States: analysis of incidence, outcome, and associated costs of care," Crit. Care Med. 29(7): 1303-10.

Asadullah et al., 1995, "Immunodepression Following Neurosurgical Procedures," Critical Care Medicine 23 (12): 1976-1983.

BD™ Cytometric Bead Array (CBA), 2004, "Human Inflammation Kit Instruction Manual," BD Biiosciences.

Belobordova et al., 2000, "Small molecules originating from microbes (SMOM) and their role in microbes-host relationship," Microb. Ecol. Health and Disease; 12:12-21.

Beutler et al., 2003, "From phenomenon to phenotype and from phenotype to gene: Forward genetics and the problem of sepsis," J. Infect. Dis. 187 (Suppl. 2): S321-26.

Bone et al., 1992, "Definitions for Sepsis and Organ Failure," Critical Care Medicine 20 (6): 724-726.

Bright et al., 2002, "Rapid typing of bacteria using matrix-assisted laser desorption ionization time-of-flight mass spectrometry and pattern recognition software," J. Microbiol. Methods 48: 127-38.

Brunkhorst et al., 2002, "Diagnostic approach to sepsis-state of the rat!," Zentralblatt fur Chirurgie; 127(3): 165-173.

Cariou et al., 2002, "The era of genomics: impact on sepsis clinical trial design," Crit. Care Med. 30 (Suppl.): S341-48.

Cheadle, 1993, "The Human Leukocyte Antigens and Their Relationship to Infection," The American Journal of Surgery 165 (2A Suppl): 75S-81S.

Chinnaiyan et al., 2001, "Molecular signatures of sepsis: multiorgan gene expression profiles of systemic inflammation," Am J Pathol. 159(4):1199-209.

Cobb et al., 2002, "Sepsis gene expression profiling: murine splenic compared with hepatic responses determined by using complementary DNA microarrays," Crit. Care Med. 30(12):2711-2721.

Creighton et al., 2003, "Expression of matrix metalloproteinase 9 (MMP-9/gelatinase B) in adenocarcinomas strongly correlated with expression of immune response genes," In Silico Biol. 3(3): 301-11.

Dalluge, 2000, "Mass spectrometry for direct determination of proteins in cells: applications in biotechnology and microbiology," Fresenius J. Anal. Chem. 366: 701-11.

DeBont et al., 1999, "Plasma IL-8 and IL-6 Levels can be used to Define a Group of Low Risk of Septicaemia Among Cancer Patients with Fever and Neurtopenia," British Journal of Haematology 107: 375-380.

Ditschkowski et al., 1999, "HLA-DR Expression and Soluble HLA-DR Levels in Septic Patients after Trauma," Annals of Surgery 229 (2): 246-254.

Dollner et al., 2001, "Early diagnostic markers for neonatal sepsis: Comparing C-reactive protein, interleukin -6, soluble tumour necrosis factor receptors and soluble adhesion molecules," J Clin Epidemiol; 54(12):1251-7.

Drobnik et al., 2003, "Plasma ceramide and lysophosphatidylcholine inversely correlate with mortality in sepsis patients," J Lipid Res; 44(4):754-61.

Feezor et al., 2003, "Molecular Characterization of the Acute Inflammatory Response to Infections with Gram-Negative versus Gram-Positive Bacteria," Infect Immun; 71(10):5803-13.

Fung et al., 2002, "ProteinChip® Clinical Proteomics: Computational Challenges and Solutions," Biotechniques; Suppl:34-8, 40-1.

Gagnon et al., 2002, "Endoplasmic reticulum-mediated phagocytosis is a mechanism of entry into macrophages," Cell 110: 119-31.

Gaut et al., 2001, "Neutrophils employ the myeloperoxidase system to generate antimicrobial brominating and chlorinating oxidants during sepsis," Proc Natl Acad Sci U S A; 98(21):11961-6.

Giannoudis et al., 1998, "Stimulation of Inflammatory Markers after Blunt Trauma," British Journal of Surgery 85: 986-990.

Groeneveld et al., 2001, "Circulating inflammatory mediators in patients with fever: predicting bloodstream infection," Clin. Diag. Lab. Immunol. 8(6): 1189-95.

Hagberg, 1998, "From magnetic resonance spectroscopy to classification of tumors: a review of pattern recognition methods," NMR Biomed. 11: 148-56.

Harbarth et al., 2001, "Diagnostic value of procalcitonin, interleukin-6, and interleukin-8 in critically ill patients admitted with suspected sepsis," Am J Respir Crit Care Med; 164(3):396-402.

Harper, Pyrolysis and GC in Polymer Analysis (Marcel Dekker, Inc. 1985).

Hastie et al., The Elements of Statistical Learning (Springer-Verlag 2001).

Healy, 2002, "New and emerging therapies for sepsis," Annuls Pharmacother. 36: 648-54.

Joyce et al., 2001, "Gene Expression Profile of antithromtotic protein C defines new mechanisms modulating inflammation and apoptosis," J. Biol. Chem. 276(14): 11,199-203.

Karzai et al., 1998, "Sepsis: definitions and diagnosis," Int'l J. Crit. Practice 95 (Suppl.): 44-48.

Knaus et al., 1991, "The Apache III Prognostic System—Risk Prediction of Hospital Morality for Critically Ill Hospitalized Adults," Chest 100 (6): 1619-1636.

Kuster et al., 1998, "Interleukin-1 receptor antagonist and interleukin-6 for early diagnosis of neonatal sepsis 2 days before clinical manifestation," Lancet 352(9136):1271-1277.

Lam et al., 2003, "Time course of early and late changes in plasma DNA in trauma patients," Clin. Chem. 49(8): 1286-91.

Llewelyn et al., 2001, "Diagnosis of infection in sepsis," Intensive Care Med. 27: S10-S32.

Manjuck et al., 2000, "Decreased Response to Recall Antigens is Associated with Depressed Costimulatory Receptor Expression in Septic Critically Ill Patients," Journal Laboratory Clinical Medicine 135 (2): 153-160.

Marshall et al., 2003, "Measures, markers, and mediators: Toward a staging system for clinical sepsis. A report from the Fifth Toronto Sepsis Roundtable, Toronto, Ontario, Canada, Oct. 25-26, 2000," Crit. Care Med. 31(5): 1560-67.

Members Of The American College Of Chest Physicians/Society Of Critical Care Medicine Consensus Conference Committee, 1992, "American College of Chest Physicians/Society of Critical Care Medicine Consensus Conference: definitions for sepsis and organ failure and guidelines for the use of innovative therapies in sepsis," Crit. Care Med. 20(6): 864-74.

Millili et al., 1998, "Predicting Surgical Outcome Using Bayesian Analysis," Journal of Surgical Research 77: 45-49.

Muller et al., 2000, "Calcitonin Precursors are Reliable Markers of Sepsis in a Medical Intensive Care Unit," Critical Care Medicine 4: 977-983.

Muret et al., 2000, "Ex vivo T-lymphocyte derived cytokine production in SIRS patients is influenced by experimental procedures", Shock 13(3): 169-74.

Nadel, 2002, "Helping to understand studies examining genetic susceptibility to sepsis," Clin. Exp. Immunol. 127: 191-92.

Natanson et al., 1998, "The sirens' songs of confirmatory sepsis trials: selection bias and sampling error," Crit. Care Med. 26(12): 1927-31.

Nupponen et al., 2001, "Neutrophil CD11b Expression and Circulating Interleukin-8 as Diagnostic Markers for Early-Onset Neonatal Sepsis," Pediatrics 108 (1): 1-6.

Oberholzer et al., 2001, "Sepsis syndromes: understanding the role of innate and acquired immunity," Shock 16: 83-96.

Oczenski, 2003, "HLA-DR as a Marker for Increased Risk for Systemic Inflammation and Septic Complications after Cardiac Surgery," Intensive Care Medicine 29: 1253-1257.

Paterson et al., 2002, "Sepsis and the systemic inflammatory response syndrome," J.R. Col.. Surg. Edinb. 127: 191-92.

Pathan et al., 2003, "The complexity of the inflammatory response to the meningococcal sepsis revealed by gene expression profiling using cDNA microarrays," Crit. Care Med; 31(12 Suppl.): A47.

Perry et al., 2003, "Is Low Monocyte HLA-DR Expression Helpful to Predict Outcome in Severe Sepsis?" Intensive Care Medicine 29: 1245-1252.

Petricoin et al., 2002, "Use of proteomic patterns in serum to identify ovarian cancer," Lancet 359: 572-77.

Presto Elgstoen et al., 2001, "Potential of capillary electrophoresis, tandem mass spectrometry and coupled capillary electrophoresis-tandem mass spectrometry as diagnostic tools," J. Chromatogr. A; 914: 265-275.

Rangel-Frausto et al., 1995, "The natural history of the systemic inflammatory response syndrome (SIRS)," J. Am. Med. Ass'n. 273: 117-23.

Rangel-Frautso et al., 1998, "The Dynamics of Disease Progression in Sepsis: Markov Modeling Describing the Natural History and the Likely Impast of Effective Antisepsis Agents," Clinical Infectious Diseases 27: 185-190.

Reinhart et al., 2002, "Markers of endothelial damage in organ dysfunction and sepsis, "Crit. Care Med. 30(5): S302-12.

Rixen et al., 1996, "Sepsis/SIRS', Physiologic Classification, Severity Stratification, Relation to Cytokine Elaboration and Outcome Prediction in Posttrauma Illness," J. Trauma 41(4): 581-598.

Roumen et al., 1993, "Scoring systems and blood lactate concentrations in relation to the development of Adult Respiratory Distress Syndrome and Multiple Organ Failure in severely traumatized patients," J. Trauma 35(3): 349-55.

Sambrook et al., Molecular Cloning ($3^{rd}$ ed., Cold Spring Harbor Laboratory Press 2001).

Sauaia et al., 1994, "Early Predictors of Postinjury Multiple Organ Failure," Arch. Surgery 129: 39-45.

Selberg et al., 2000, "Discrimination of Sepsis and Systematic Inflammatory Response Syndrome by Determination of Circulating Plasma Concentrations of Procalcitonin, Protein Complement 3a, and Interleukin-6," Crit. Care Med. 28 (i): 2793-2798.

Shoemaker et al., 2002, "Recent developments in DNA microarrays," Curr. Opinion Microbiol. 5: 334-37.

Slotman et al., 2002, "Prospectively Validated Prediction of Physiologic Variables and Organ Failure in Septic Patents: The Systemic Mediator Associated Response Test (SMART)," Critical Care Medicine 30 (5): 1035-1045.

Slotman et al., 1997, "Multivariate Regression Modeling for the Prediction of Inflammation, Systemic Pressure, and End-organ Function in Severe Sepsis," Shock 8 (3): 225-231.

Slotman et al., 2000, "Prospectively validated predictions of shock and organ failure in individual spetic surgical patients: the Systemic Mediator Associated Response Text," Crit. Care 2000 4(5): 319-26.

Smith et al., 2004, "Impact of immunomodulatory oligodeoxynucleotides on cytokine production in the lipopolysaccharide-stimulated human whole blood model," Surgery 136(2):464-472.

Stordeur et al., 2002, "Cytokine mRNA quantification by real-time PCR," J. Immunol. Methods 259: 55-64.

Suzuki et al., 2000, "Comprehensive gene expression profile of LPS-stimulated human monocytes by Sage," Blood; 96(7):2584-91.

Takala et al., 2002, "Markers of inflammation in sepsis," Annuls Med. 34: 614-23.

Takala et al., 1999, "Systemic inflammatory response syndrome without systemic inflammation in acutely ill patients admitted to hospital in a medical emergency," Clin. Sci. 96:287-95.

Tan et al., 2002, "The gene expression fingerprint of human heart failure," Proc. Nat'l Acad. Sci. USA 99: 11387-92.

Taniguchi et al., 1999, "Change in the Ratio of Interleukin-6 to Interleukin-10 Predicts a Poor Outcome in Patients with Systemic Inflammatory Response Syndrome," Critical Care Medicine 27 (7): 1262-1264.

Tarnok et al., 2003, "Cytometric bead array to measure six cytokines in twenty-five microliters of serum," Clin. Chem. 49(6): 1000-02.

Titus, 2003, "Latest assay opens another sepsis frontier," College of American Pathologists, CAP Today, at http://www.cap.org/apps/docs/cap_today/feature_stories/sepsis.html (posted May 2003).

Van den Berk et al., 1997, "Low HLA-DR Expression on Monocytes as a Prognostic Marker for Bacterial Sepsis after Liver Transplantation," Transplantation 63 (12): 1846-1848.

Van Leeuwen et al., 2003, "Lipoprotein metabolism in patients with severe sepsis," Crit. Care Med. 31(5): 1359-66.

Venables et al., Modern Applied Statistics with S ($4^{th}$ ed., Springer 2002).

Vincent et al., The Sepsis Text (Carlet et al., eds., Kluwer Academic Publishers 2002).

von Landenberg et al., 2001, "New approaches in the diagnosis of sepsis," Isr. Med. Assoc. J. 3: 439-42.

Wagner et al., 1994, "Daily Prognostic Estimates for Critically Ill Adults in Intensive Care Units: Results from a Prospective, Multicenter, Inception Cohort Analysis," Critical Care Medicine 22 (9): 1359-1372.

Wagner et al., 2002, "Interpretation of static time-of flight secondary ion mass spectra of adsorbed protein films by multvariate pattern recognition," Anal. Chem. 74: 1824-35.

Wagner et al., 2002, "Interpretation of static time-of-flight secondary ion mass spectra of adsorbed protein films by multivariate pattern recognition," Anal. Chem. 74: 1824-35.

Wakefield et al., 1993, "Polymorphonuclear Leukocyte Activation. An Early Marker of the Postsurgical Sepsis Response," Arch. Surg. 128: 390-395.

Wakefield et al., 1993, "Changes in Major Histocompatibility Complex Class II Expression in Monocytes and T cells of Patients Developing Infection after Surgery," British Journal of Surgery 80(2): 205-209.

Wakefield et al., 1995, "Surgery and the Release of a Neutrophil Fcy Receptor," The American Journal of Surgery 170: 277-284.

Wang et al., 1998, "Tissue coexpression of LBP and CD14 mRNA in a mouse model of sepsis," J. Surg. Res. 76(1):67-73.

Wei et al., 1999, "Desorption-ionization mass spectrometry on porous silicon," Nature 399: 243-46.

Weigand et al., 1999, "Gene Expression Pattern in Human Monocytes as a Surrogate Marker for Systemic Inflammatory Response Syndrome (SIRS)," Mol Med; 5(3):192-202.

Weinstein et al., 1997, "The clinical significance of positive blood cultures in the 1990s: a prospective comprehensive evaluation of the microbiology, epidemiology, and outcome of bacteremia and fungemia in adults," Clin. Infectious Diseases 24: 584-602.

Weirich et al., 1998, "Neutrophil CD11b Expression as a Diagnostic Marker for Early-Onset Neonatal Infection," The Journal of Pediatrics 132 (ss.3,1): 445-451.

Weglohner et al., 2001, "Isolation and characterization of serum procalcitonin from patients with sepsis," Peptides 22: 2099-2103.

Wert et al., 2000, "Increased metalloproteinase activity, oxidant production, and emphysema in surfactant protein D gene-inactivated mice," Proc. Natl. Acad. Sci. USA 97(11):5972-5977.

Zhang et al., 2001, "Recursvie partitioning for tumor classification with gene expression microarray data," Proc Natl Acad Sci U S A; 98(12):6730-5.

Zhao et al., 2001, "Human endothelial cell response to gram-negative lipopolysaccharide assessed with cDNA microarrays," Am. J. Physiol. Cell Physiol. 281(5): C1587-95 (Nov. 2001).

Zhu et al., 1997, "Effects of prolactin and metoclopramide on macrophage cytokine gene expression in late sepsis," Cytokine 9(6):437-446.

Zou, et al., 2002, "Application of cDNA microassays to generate a molecular taxonomy capable of distinguishing between colon cancer and normal colon," Oncogene 21: 4855-62.

SIRS -negative → SIRS -positive

↓

Sepsis

Severe Sepsis

↓

Septic Shock

↓

Multiple Organ Dysfunction

FIGURE 1

| Up-Regulated Proteins | | | | | | Protein Identifier | GenBank Accession Number |
|---|---|---|---|---|---|---|---|
| SIRS | | | Sepsis | | | | |
| Day 1 | T–48 hours | T 0 hours | Day 1 | T–48 hours | T 0 hours | | |
| 127 | 81 | 80 | 125 | 371 | 508 | 15990507 | AAH15642 |
| 308 | 190 | 229 | 98 | 615 | 659 | 21361198 | NP_000286 |
| 10 | 16 | 13 | 43 | 20 | 26 | 4505881 | NP_000292 |
| 35 | 15 | 16 | 23 | 25 | 39 | 2851501 | P19827 |
| 48 | 39 | 35 | 101 | 81 | 58 | 72059 | NBHUA2 |
| 62 | 44 | 29 | 20 | 47 | 68 | 4557327 | NP_000033 |
| 125 | 64 | 44 | 147 | 151 | 142 | 36308 | CAA39974 |
| 306 | 276 | 170 | 228 | 361 | 408 | 1197209 | CAA29229 |
| 22 | 201 | 317 | 169 | 702 | 519 | 1197209 | CAA29229 |
| 12 | 4 | 1 | 15 | 9 | 28 | 627517 | BAA34292 |
| 30 | 10 | 12 | 10 | 58 | 37 | 4502149 | AAHI5642 |
| 7 | 2 | 1 | 9 | 8 | 3 | 4504165 | NP_000168 |
| 33 | 37 | 25 | 50 | 43 | 67 | 2521983 | BAA22652 |
| 7 | 11 | 14 | 34 | 85 | 26 | 4504345 | NP_000508 |
| 0 | 0 | 14 | 0 | 31 | 33 | 5031777 | NP_005521 |
| 0 | 1 | 0 | 6 | 15 | 12 | 1351236 | P05543 |
| 2 | 1 | 0 | 4 | 8 | 4 | 2144886 | C1HUQB |

FIG. 7A

| GenBank Accession Number | Protein Identifier | Protein Description |
|---|---|---|
| AAH15642 | 15990507 | Similar to serine (or cysteine) proteinase inhibitor, clade A (α−1 antiproteinase, antitrypsin), member 1 |
| NP_000286 | 21361198 | Similar to serine (or cysteine) proteinase inhibitor, clade A (α-1 antiproteinase, antitrypsin), member 1 |
| NP_000292 | 4505881 | Plasminogen precursor [Contains Angiostatin] |
| P19827 | 2851501 | Inter- α −trypsin inhibitor heavy chain H1 precursor (ITI heavy chain H1) (Serum-derived hyaluronan-associated protein) (SHAP) |
| NBHUA2 | 72059 | Leucine-rich α −2-glycoprotein |
| NP_000033 | 4557327 | Apolipoprotein H precursor |
| CAA39974 | 36308 | SAAB1 β |
| CAA29229 | 1197209 | α −1-acid glycoprotein 1 precursor |
| CAA29229 | 1197209 | α −1-acid glycoprotein |
| BAA34292 | 627517 | Lipopolysaccharide-binding protein |
| AAH15642 | 4502149 | Apolipoprotein A-II precursor (Apo-AII) (ApoA-II) |
| NP_000168 | 4504165 | Gelsolin precursor, plasma (Actin-depolymerizing factor) (ADF) (Brevin) (AGEL) |
| BAA22652 | 2521983 | α 2-HS glycoprotein |
| NP_000508 | 4504345 | Hemoglobin α chain |
| NP_005521 | 5031777 | Isocitrate dehydrogenase [NAD] subunit α, mitochondrial precursor (Isocitric dehydrogenase) |
| P05543 | 1351236 | Thyroxine-binding globulin precursor (T4-binding globulin) |
| C1HUQB | 2144886 | Complement subcomponent C1q chain B precursor |

FIGURE 7B

| Down-Regulated Proteins |||||| Protein Identifier | GenBank Accession Number |
|---|---|---|---|---|---|---|---|
| SIRS ||| Sepsis ||| | |
| Day 1 | T−48 hours | T 0 hours | Day 1 | T−48 hours | T 0 hours | | |
| 72 | 49 | 39 | 40 | 9 | 18 | 4504489 | NP_000403 |
| 17 | 55 | 26 | 15 | 16 | 9 | 4502261 | NP_000479 |
| 0 | 18 | 23 | 19 | 2 | 1 | 13376417 | NP_079216 |
| 16 | 6 | 3 | 5 | 0 | 0 | 19344010 | AAH25681 |
| 8 | 5 | 5 | 7 | 1 | 2 | 18490598 | AAH22256 |
| 21 | 10 | 6 | 4 | 3 | 5 | 15705411 | AAL05629 |
| 16 | 10 | 0 | 3 | 0 | 2 | 4505047 | NP_002336 |
| 12 | 17 | 6 | 0 | 5 | 4 | 4557323 | NP_000031 |
| 13 | 15 | 9 | 6 | 0 | 0 | 4502157 | NP_001636 |
| 0 | 9 | 16 | 4 | 0 | 0 | 3868933 | BAA34292 |
| 5 | 10 | 10 | 2 | 2 | 0 | 13169436 | AAK13574 |
| 4 | 5 | 2 | 0 | 0 | 0 | 14009346 | AAK50336 |
| 3 | 8 | 0 | 0 | 0 | 1 | 21040475 | AAH30580 |
| 3 | 1 | 9 | 1 | 0 | 0 | 6912502 | NP_036346 |
| 24 | 35 | 6 | 6 | 2 | 4 | 27697129 | AAH41761 |

FIG. 8A

| GenBank Accession Number | Protein Identifier | Protein Description |
|---|---|---|
| NP_000403 | 4504489 | Histidine-rich glycoprotein precursor (Histidine-proline rich glycoprotein) (HPRG) |
| NP_000479 | 4502261 | Serine (or cysteine) proteinase inhibitor, clade C (antithrombin), member 1; Antithrombin-III precursor (ATIII) (PRO0309) |
| NP_079216 | 13376417 | Unnamed protein product |
| AAH25681 | 19344010 | Insulin-like growth factor binding protein, acid labile subunit |
| AAH22256 | 18490598 | Lipopolysaccharide binding protein |
| AAL05629 | 15705411 | Peptidoglycan recognition protein L precursor |
| NP_002336 | 4505047 | Lumican precursor (Keratan sulfate proteoglycan lumican) (KSPG lumican) |
| NP_000031 | 4557323 | Apolipoprotein C-III precursor (Apo-CIII) |
| NP_001636 | 4502157 | Apolipoprotein C-I precursor (Apo-CI) |
| BAA34292 | 3868933 | α1-acid glycoprotein |
| AAK13574 | 13169436 | Forkhead homolog |
| AAK50336 | 14009346 | nGAP-like protein |
| AAH30580 | 21040475 | Unknown (protein for MGC:26123) |
| NP_036346 | 6912502 | UDP-GlcNAc:α-1,3-D-mannoside β-1,4-N-acetylglucosaminyltransferase IV |
| AAH41761 | 27697129 | Similar to dedicator of cyto-kinesis 1 |

FIGURE 8B

MASS SPECTROMETRY TECHNIQUES FOR DETERMINING THE STATUS OF SEPSIS IN AN INDIVIDUAL

RELATED APPLICATIONS

This application is a continuation of U.S. patent application Ser. No. 10/704,758, filed Nov. 12, 2003, now abandoned which claims priority to U.S. Provisional Patent Application Ser. No. 60/425,322, filed Nov. 12, 2002, and to U.S. Provisional Patent Application Ser. No. 60/503,548, filed Sep. 17, 2003. U.S. Provisional Patent Application Ser. No. 60/425, 322, filed Nov. 12, 2002, and U.S. Provisional Patent Application Ser. No. 60/503,548, filed Sep. 17, 2003, are each hereby incorporated by reference herein in their entirety.

FIELD OF THE INVENTION

The present invention relates to mass spectrometry techniques for diagnosing or predicting sepsis or its stages of progression in an individual. The present invention also relates to mass spectrometry methods for diagnosing systemic inflammatory response syndrome in an individual.

BACKGROUND OF THE INVENTION

Early detection of a disease condition typically allows for a more effective therapeutic treatment with a correspondingly more favorable clinical outcome. In many cases, however, early detection of disease symptoms is problematic; hence, a disease may become relatively advanced before diagnosis is possible. Systemic inflammatory conditions represent one such class of diseases. These conditions, particularly sepsis, typically result from an interaction between a pathogenic microorganism and the host's defense system that triggers an excessive and dysregulated inflammatory response in the host. The complexity of the host's response during the systemic inflammatory response has complicated efforts towards understanding disease pathogenesis. (Reviewed in Healy, Annul. Pharmacother. 36: 648-54 (2002).) An incomplete understanding of the disease pathogenesis, in turn, contributes to the difficulty in finding diagnostic biomarkers. Early and reliable diagnosis is imperative, however, because of the remarkably rapid progression of sepsis into a life-threatening condition.

Sepsis follows a well-described time course, progressing from systemic inflammatory response syndrome ("SIRS") -negative to SIRS-positive to sepsis, which may then progress to severe sepsis, septic shock, multiple organ dysfunction ("MOD"), and ultimately death. Sepsis also may arise in an infected individual when the individual subsequently develops SIRS. "SIRS" is commonly defined as the presence of two or more of the following parameters: body temperature greater than 38° C. or less than 36° C.; heart rate greater than 90 beats per minute; respiratory rate greater than 20 breaths per minute; $P_{CO2}$ less than 32 mm Hg: and a white blood cell count either less than $4.0 \times 10^9$ cells/L or greater than $12.0 \times 10^9$ cells/L, or having greater than 10% immature band forms. "Sepsis" is commonly defined as SIRS with a confirmed infectious process. "Severe sepsis" is associated with MOD, hypotension, disseminated intravascular coagulation ("DIC") or hypoperfusion abnormalities, including lactic acidosis, oliguria, and changes in mental status. "Septic shock" is commonly defined as sepsis-induced hypotension that is resistant to fluid resuscitation with the additional presence of hypoperfusion abnormalities.

Documenting the presence of the pathogenic microorganisms clinically significant to sepsis has proven difficult. Causative microorganisms typically are detected by culturing a patient's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of patients presenting clinical manifestations of sepsis. (Rangel-Frausto et al., JAMA 273: 117-23 (1995).) Diagnosis can be further complicated by contamination of samples by non-pathogenic microorganisms. For example, only 12.4% of detected microorganisms were clinically significant in a study of 707 patients with septicemia. (Weinstein et al., Clinical Infectious Diseases 24: 584-602 (1997).)

The difficulty in early diagnosis of sepsis is reflected by the high morbidity and mortality associated with the disease. Sepsis currently is the tenth leading cause of death in the United States and is especially prevalent among hospitalized patients in non-coronary intensive care units (ICUs), where it is the most common cause of death. The overall rate of mortality is as high as 35%, with an estimated 750,000 cases per year occurring in the United States alone. The annual cost to treat sepsis in the United States alone is in the order of billions of dollars.

A need, therefore, exists for a method of diagnosing sepsis sufficiently early to allow effective intervention and prevention. Most existing sepsis scoring systems or predictive models predict only the risk of late-stage complications, including death, in patients who already are considered septic. Such systems and models, however, do not predict the development of sepsis itself. What is particularly needed is a way to categorize those patients with SIRS who will or will not develop sepsis. Currently, researchers will typically define a single biomarker that is expressed at a different level in a group of septic patients versus a normal (i.e., non-septic) control group of patients. U.S. patent application Ser. No. 10/400,275, filed Mar. 26, 2003, the entire contents of which are hereby incorporated by reference, discloses a method of indicating early sepsis by analyzing time-dependent changes in the expression level of various biomarkers. Accordingly, optimal methods of diagnosing early sepsis currently require both measuring a plurality of biomarkers and monitoring the expression of these biomarkers over a period of time.

There is a continuing urgent need in the art to diagnose sepsis with specificity and sensitivity, without the need for monitoring a patient over time. Ideally, diagnosis would be made by a technique that accurately, rapidly, and simultaneously measures a plurality of biomarkers at a single point in time, thereby minimizing disease progression during the time required for diagnosis.

SUMMARY OF THE INVENTION

The present invention allows for accurate, rapid, and sensitive prediction and diagnosis of sepsis through a measurement of more than one biomarker taken from a biological sample at a single point in time. This is accomplished by obtaining a biomarker profile at a single point in time from an individual, particularly an individual at risk of developing sepsis, having sepsis, or suspected of having sepsis, and comparing the biomarker profile from the individual to a reference biomarker profile. The reference biomarker profile may be obtained from a population of individuals (a "reference population") who are, for example, afflicted with sepsis or who are suffering from either the onset of sepsis or a particular stage in the progression of sepsis. If the biomarker profile from the individual contains appropriately characteristic features of the biomarker profile from the reference population, then the individual is diagnosed as having a more likely chance of becoming septic, as being afflicted with sepsis or as being at the particular stage in the progression of sepsis as the reference population. The reference biomarker profile may also be obtained from various populations of individuals including those who are suffering from SIRS or those who are suffering from an infection but who are not suffering from SIRS. Accordingly, the present invention allows the clinician to determine, inter alia, those patients who do not have SIRS, who have. SIRS but are not likely to develop sepsis within the time frame of the investigation, who have sepsis, or who are at risk of eventually becoming septic.

Although the methods of the present invention are particularly useful for detecting or predicting the onset of sepsis in SIRS patients, one of ordinary skill in the art will understand that the present methods may be used for any patient including, but not limited to, patients suspected of having SIRS or of being at any stage of sepsis. For example, a biological sample could be taken from a patient, and a profile of biomarkers in the sample could be compared to several different reference biomarker profiles, each profile derived from individuals such as, for example, those having SIRS or being at a particular stage of sepsis. Classification of the patient's biomarker profile as corresponding to the profile derived from a particular reference population is predictive that the patient falls within the reference population. Based on the diagnosis resulting from the methods of the present invention, an appropriate treatment regimen could then be initiated.

Existing methods for the diagnosis or prediction of SIRS, sepsis or a stage in the progression of sepsis are based on clinical signs and symptoms that are nonspecific; therefore, the resulting diagnosis often has limited clinical utility. Because the methods of the present invention accurately detect various stages of sepsis, they can be used to identify those individuals who might appropriately be enrolled in a therapeutic study. Because sepsis may be predicted or diagnosed from a "snapshot" of biomarker expression in a biological sample obtained at a single point in time, this therapeutic study may be initiated before the onset of serious clinical symptoms. Because the biological sample is assayed for its biomarker profile, identification of the particular biomarkers is unnecessary. Nevertheless, the present invention provides methods to identify specific biomarkers of the profiles that are characteristic of sepsis or of a particular stage in the progression of sepsis. Such biomarkers themselves will be useful tools in predicting or diagnosing sepsis.

Accordingly, the present invention provides, inter alia, methods of predicting the onset of sepsis in an individual. The methods comprise obtaining a biomarker profile at a single point in time from the individual and comparing the individual's biomarker profile to a reference biomarker profile. Comparison of the biomarker profiles can predict the onset of sepsis in the individual with an accuracy of at least about 60%. This method may be repeated again at any time prior to the onset of sepsis.

The present invention also provides a method of diagnosing sepsis in an individual having or suspected of having sepsis comprising obtaining a biomarker profile at a single point in time from the individual and comparing the individual's biomarker profile to a reference biomarker profile. Comparison of the biomarker profiles can diagnose sepsis in the individual with an accuracy of at least about 60%. This method may be repeated on the individual at any time.

The present invention further provides a method of determining the progression (i.e., the stage) of sepsis in an individual having or suspected of having sepsis. This method comprises obtaining a biomarker profile at a single point in time from the individual and comparing the individual's biomarker profile to a reference biomarker profile. Comparison of the biomarker profiles can determine the progression of sepsis in the individual with an accuracy of at least about 60%. This method may also be repeated on the individual at any time.

Additionally, the present invention provides a method of diagnosing SIRS in an individual having or suspected of having SIRS. This method comprises obtaining a biomarker profile at a single point in time from the individual and comparing the individual's biomarker profile to a reference biomarker profile. Comparison of the biomarker profiles can diagnose SIRS in the individual with an accuracy of at least about 60%. This method may also be repeated on the individual at any time.

In another embodiment, the invention provides, inter alia, a method of determining the status of sepsis or diagnosing SIRS in an individual comprising applying a decision rule. The decision rule comprises comparing (i) a biomarker profile generated from a biological sample taken from the individual at a single point in time with (ii) a biomarker profile generated from a reference population. Application of the decision rule determines the status of sepsis or diagnoses SIRS in the individual. The method may be repeated on the individual at one or more separate, single points in time.

The present invention further provides, inter alia, a method of determining the status of sepsis or diagnosing SIRS in an individual comprising obtaining a biomarker profile from a biological sample taken from the individual and comparing the individual's biomarker profile to a reference biomarker profile. A single such comparison is capable of classifying the individual as having membership in the reference population. Comparison of the biomarker profile determines the status of sepsis or diagnoses SIRS in the individual.

The invention further provides, inter alia, a method of determining the status of sepsis or diagnosing SIRS in an individual comprising obtaining a biomarker profile from a biological sample taken from the individual and comparing the individual's biomarker profile to a reference biomarker profile obtained from biological samples from a reference population. The reference population may be selected from the group consisting of a normal reference population, a SIRS-positive reference population, an infected/SIRS-negative reference population, a sepsis-positive reference population, a reference population at a particular stage in the progression of sepsis, a SIRS-positive reference population that will be confirmed as having sepsis by conventional techniques after about 0-36 hours, a SIRS-positive reference population that will be confirmed as having sepsis by conventional techniques after about 36-60 hours, and a SIRS-positive reference population that will be confirmed as having sepsis by conventional techniques after about 60-84 hours. A single such comparison is capable of classifying the individual as having membership in the reference population, and the comparison determines the status of sepsis or diagnoses SIRS in the individual.

In yet another embodiment, the present invention provides, inter alia, a method of determining the status of sepsis or diagnosing SIRS in an individual. The method comprises comparing a measurable characteristic of at least one biomarker between a biomarker profile obtained from a biological sample from the individual and a biomarker profile obtained from biological samples from a reference population. Based on this comparison, the individual is classified as belonging to or not belonging to the reference population. The comparison, therefore, determines the status of sepsis or diagnoses SIRS in the individual. The biomarkers, in one embodiment, are selected from the group of biomarkers shown in any one of TABLES 2-13.

In a further embodiment, the present invention provides, inter alia, a method of determining the status of sepsis or diagnosing SIRS in an individual comprising selecting at least two features from a set of biomarkers in a profile generated from a biological sample of an individual. These features are compared to a set of the same biomarkers in a profile generated from biological samples from a reference population. A single such comparison is capable of classifying the individual as having membership in the reference population with an accuracy of at least about 60%, and the comparison determines the status of sepsis or diagnoses SIRS in the individual.

The present invention also provides, inter alia, a method of determining the status of sepsis or diagnosing SIRS in an individual comprising determining the changes in the abundance of at least two biomarkers contained in a biological sample of an individual and comparing the abundance of these biomarkers in the individual's sample to the abundance of these biomarkers in biological samples from a reference population. The comparison is capable of classifying the individual as having membership in the reference population, and the comparison determines the status of sepsis or diagnoses SIRS in the individual.

In another embodiment, the invention provides, inter alia, a method of determining the status of sepsis in an individual, comprising determining changes in the abundance of at least one, two, three, four, five, 10 or 20 biomarkers as compared to changes in the abundance of the at least one, two, three, four, five, 10 or 20 biomarkers for biological samples from a reference population that contracted sepsis and one that did not. The biomarkers are selected from the group consisting of the biomarkers listed in any one of TABLES 2-13. Alternatively, the abundance of the at least one, two, three, four, five, 10 or 20 biomarkers may be compared to the abundance of the at least one, two, three, four, five, 10 or 20 biomarkers.

The present invention further provides, inter alia, a method of isolating a biomarker, the presence of which in a biological sample is diagnostic or predictive of sepsis. This method comprises obtaining a reference biomarker profile from a population of individuals and identifying a feature of the reference biomarker profile that is predictive or diagnostic of sepsis or one of the stages in the progression of sepsis. This method further comprises identifying a biomarker that corresponds with the feature and then isolating the biomarker.

In another embodiment, the present invention provides a kit comprising at least one, two, three, four, five, 10 or all of the biomarkers selected from the group consisting of the biomarkers listed in any one of TABLES 2-13.

In another embodiment, the reference biomarker profile may comprise a combination of at least two features, preferably five, 10, or 20 or more, where the features are characteristics of biomarkers in the sample. In this embodiment, the features will contribute to the prediction of the inclusion of an individual in a particular reference population. The relative contribution of the features in predicting inclusion may be determined by a data analysis algorithm that predicts class inclusion with an accuracy of at least about 60%, at least about 70%, at least about 80%, at least about 90%, about 95%, about 96%, about 97%, about 98%, about 99% or about 100%. In one embodiment, the combination of features allows the prediction of the onset of sepsis about 24, about 48, or about 72 hours prior to the actual onset of sepsis, as determined using conventional techniques.

In yet another embodiment, the reference biomarker profile may comprise at least two features, at least one of which is characteristic of the corresponding biomarker and where the feature will allow the prediction of inclusion of an individual in a sepsis-positive or SIRS-positive population. In this embodiment, the feature is assigned a p-value, which is obtained from a nonparametric test, such as a Wilcoxon Signed Rank Test, that is directly related to the degree of certainty with which the feature can classify an individual as belonging to a sepsis-positive or SIRS-positive population. In another embodiment, the feature classifies an individual as belonging to a sepsis-positive or SIRS-positive population with an accuracy of at least about 60%, about 70%, about 80%, or about 90%. In still another embodiment, the feature allows the prediction of the onset of sepsis about 24, about 48, or about 72 hours prior to the actual onset of sepsis, as determined using conventional techniques.

In yet another embodiment, the present invention provides an array of particles, with capture molecules attached to the surface of the particles that can bind specifically to at least one, two, three, four, five, 10 or all of the biomarkers selected from the group consisting of the biomarkers listed in any one of TABLES 2-13.

BRIEF DESCRIPTION OF THE DRAWINGS

FIG. 1 illustrates the progression of SIRS to sepsis. The condition of sepsis consists of at least three stages, with a septic patient progressing from severe sepsis to septic shock to multiple organ dysfunction.

FIG. 4A shows changes in the presence in the ion in various populations of individuals who developed sepsis. Clinical suspicion of sepsis in the sepsis group occurred at "time 0," as measured by conventional techniques. "Time—24 hours" and "time—48 hours" represent samples taken about 24 hours and about 48 hours, respectively, preceding the clinical suspicion of the onset of sepsis in the sepsis group. Individuals entered the study at "Day 1. " FIG. 4B shows the presence of the same ion in samples taken from populations of individuals who did not develop sepsis at time 0.

FIGS. 7A and 7B show proteins that are regulated at higher levels in plasma up to 48 hours before conversion to sepsis.

FIGS. 8A and 8B show proteins that are regulated at lower levels in plasma up to 48 hours before conversion to sepsis.

DETAILED DESCRIPTION OF THE PREFERRED EMBODIMENTS

Figure 2:
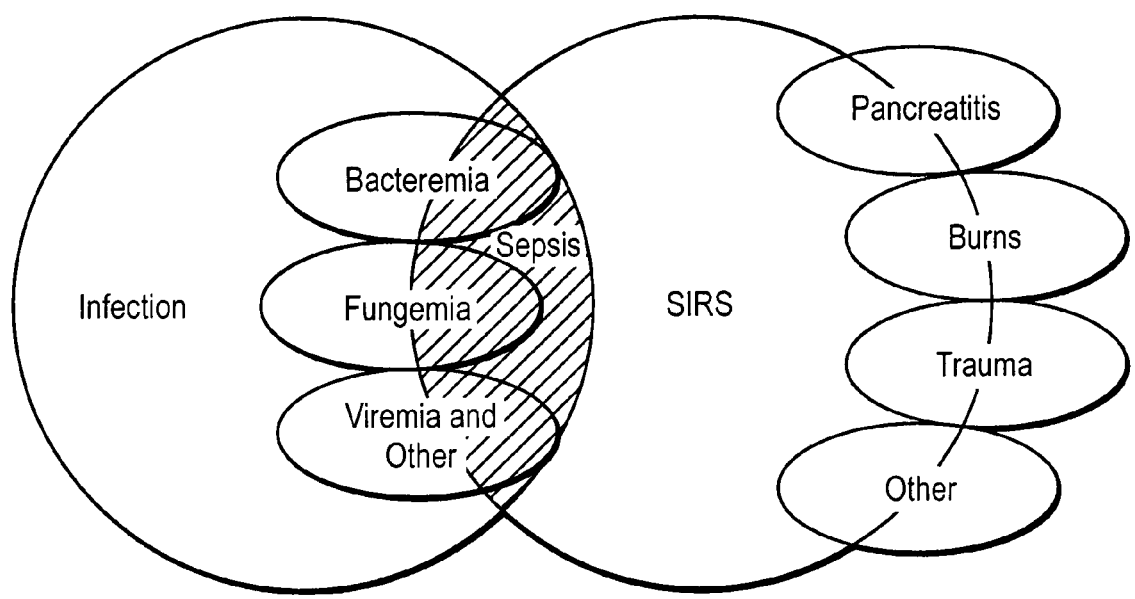
FIG. 2 shows the relationship between sepsis and SIRS. The various sets shown in the Venn diagram correspond to populations of individuals having the indicated condition.

The present invention allows for the rapid, sensitive, and accurate diagnosis or prediction of sepsis using one or more biological samples obtained from an individual at a single time point ("snapshot") or during the course of disease progression. Advantageously, sepsis may be diagnosed or predicted prior to the onset of clinical symptoms, thereby allowing for more effective therapeutic intervention.

"Systemic inflammatory response syndrome," or "SIRS," refers to a clinical response to a variety of severe clinical insults, as manifested by two or more of the following conditions within a 24-hour period:

body temperature greater than 38° C. (100.4° F.) or less than 36° C. (96.8° F.);

heart rate (HR) greater than 90 beats/minute;

respiratory rate (RR) greater than 20 breaths/minute, or $P_{CO_2}$ less than 32 mm Hg, or requiring mechanical ventilation; and white blood cell count (WBC) either greater than $12.0 \times 10^9$/L or less than $4.0 \times 10^9$/L or having greater than 10% immature forms (bands).

These symptoms of SIRS represent a consensus definition of SIRS that may be modified or supplanted by an improved definition in the future. The present definition is used to clarify current clinical practice and does not represent a critical aspect of the invention.

A patient with SIRS has a clinical presentation that is classified as SIRS, as defined above, but is not clinically deemed to be septic. Individuals who are at risk of developing sepsis include patients in an ICU and those who have otherwise suffered from a physiological trauma, such as a burn or other insult. "Sepsis" refers to a SIRS-positive condition that is associated with a confirmed infectious process. Clinical suspicion of sepsis arises from the suspicion that the SIRS-positive condition of a SIRS patient is a result of an infectious process. As used herein, "sepsis" includes all stages of sepsis including, but not limited to, the onset of sepsis, severe sepsis and MOD associated with the end stages of sepsis.

The "onset of sepsis" refers to an early stage of sepsis, i.e., prior to a stage when the clinical manifestations are sufficient to support a clinical suspicion of sepsis. Because the methods of the present invention are used to detect sepsis prior to a time that sepsis would be suspected using conventional techniques, the patient's disease status at early sepsis can only be confirmed retrospectively, when the manifestation of sepsis is more clinically obvious. The exact mechanism by which a patient becomes septic is not a critical aspect of the invention. The methods of the present invention can detect changes in the biomarker profile independent of the origin of the infectious process. Regardless of how sepsis arises, the methods of the present invention allow for determining the status of a patient having, or suspected of having, sepsis or SIRS, as classified by previously used criteria.

"Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status. "Septic shock" refers to sepsis-induced hypotension that is not responsive to adequate intravenous fluid challenge and with manifestations of peripheral hypoperfusion. A "converter patient" refers to a SIRS-positive patient who progresses to clinical suspicion of sepsis during the period the patient is monitored, typically during an ICU stay. A "non-converter patient" refers to a SIRS-positive patient who does not progress to clinical suspicion of sepsis during the period the patient is monitored, typically during an ICU stay.

A "biomarker" is virtually any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, and a small molecule that are present in the biological sample and that may be isolated from, or measured in, the biological sample. Furthermore, a biomarker can be the entire intact molecule, or it can be a portion thereof that may be partially functional or recognized, for example, by an antibody or other specific binding protein. A biomarker is considered to be informative if a measurable aspect of the biomarker is associated with a given state of the patient, such as a particular stage of sepsis. Such a measurable aspect may include, for example, the presence, absence, or concentration of the biomarker in the biological sample from the individual and/or its presence as part of a profile of biomarkers. Such a measurable aspect of a biomarker is defined herein as a "feature." A feature may also be a ratio of two or more measurable aspects of biomarkers, which biomarkers may or may not be of known identity, for example. A "biomarker profile" comprises at least two such features, where the features can correspond to the same or different classes of biomarkers such as, for example, a nucleic acid and a carbohydrate. A biomarker profile may also comprise at least three, four, five, 10, 20, 30 or more features. In one embodiment, a biomarker profile comprises hundreds, or even thousands, of features. In another embodiment, the biomarker profile comprises at least one measurable aspect of at least one internal standard.

A "phenotypic change" is a detectable change in a parameter associated with a given state of the patient. For instance, a phenotypic change may include an increase or decrease of a biomarker in a bodily fluid, where the change is associated with sepsis or the onset of sepsis. A phenotypic change may further include a change in a detectable aspect of a given state of the patient that is not a change in a measurable aspect of a biomarker. For example, a change in phenotype may include a detectable change in body temperature, respiration rate, pulse, blood pressure, or other physiological parameter. Such changes can be determined via clinical observation and measurement using conventional techniques that are well-known to the skilled artisan. As used herein, "conventional techniques" are those techniques that classify an individual based on phenotypic changes without obtaining a biomarker profile according to the present invention.

A "decision rule" is a method used to classify patients. This rule can take on one or more forms that are known in the art, as exemplified in Hastie et al., in "The Elements of Statistical Learning," Springer-Verlag (Springer, N.Y. (2001)), herein incorporated by reference in its entirety. Analysis of biomarkers in the complex mixture of molecules within the sample generates features in a data set. A decision rule may be used to act on a data set of features to, inter alia, predict the onset of sepsis, to determine the progression of sepsis, to diagnose sepsis, or to diagnose SIRS.

The application of the decision rule does not require perfect classification. A classification may be made with at least about 90% certainty, or even more, in one embodiment. In other embodiments, the certainty is at least about 80%, at least about 70%, or at least about 60%. The useful degree of certainty may vary, depending on the particular method of the present invention. "Certainty" is defined as the total number of accurately classified individuals divided by the total number of individuals subjected to classification. As used herein, "certainty" means "accuracy." Classification may also be characterized by its "sensitivity." The "sensitivity" of classification relates to the percentage of sepsis patients who were correctly identified as having sepsis. "Sensitivity" is defined in the art as the number of true positives divided by the sum of true positives and false negatives. In contrast, the "specificity" of the method is defined as the percentage of patients who were correctly identified as not having sepsis. That is, "specificity" relates to the number of true negatives divided by the sum of true negatives and false positives. In one embodiment, the sensitivity and/or specificity is at least 90%, at least 80%, at least 70% or at least 60%. The number of features that may be used to classify an individual with adequate certainty is typically about four. Depending on the degree of certainty sought, however, the number of features may be more or less, but in all cases is at least one. In one embodiment, the number of features that may be used to classify an individual is optimized to allow a classification of an individual with high certainty.

"Determining the status" of sepsis or SIRS in a patient encompasses classification of a patient's biomarker profile to (1) detect the presence of sepsis or SIRS in the patient, (2) predict the onset of sepsis or SIRS in the patient, or (3) measure the progression of sepsis in a patient. "Diagnosing" sepsis or SIRS means to identify or detect sepsis or SIRS in the patient. Because of the greater sensitivity of the present invention to detect sepsis before an overtly observable clinical manifestation, the identification or detection of sepsis includes the detection of the onset of sepsis, as defined above. That is, "predicting the onset of sepsis" means to classify the patient's biomarker profile as corresponding to the profile derived from individuals who are progressing from a particular stage of SIRS to sepsis or from a state of being infected to sepsis (i.e., from infection to infection with concomitant SIRS). "Detecting the progression" or "determining the progression" of sepsis or SIRS means to classify the biomarker profile of a patient who is already diagnosed as having sepsis or SIRS. For instance, classifying the biomarker profile of a patient who has been diagnosed as having sepsis can encompass detecting or determining the progression of the patient from sepsis to severe sepsis or to sepsis with MOD.

According to the present invention; sepsis may be diagnosed or predicted by obtaining a profile of biomarkers from a sample obtained from an individual. As used herein, "obtain" means "to come into possession of." The present invention is particularly useful in predicting and diagnosing sepsis in an individual who has an infection, or even sepsis, but who has not yet been diagnosed as having sepsis, who is suspected of having sepsis, or who is at risk of developing sepsis. In the same manner, the present invention may be used to detect and diagnose SIRS in an individual. That is, the present invention may be used to confirm a clinical suspicion of SIRS. The present invention also may be used to detect various stages of the sepsis process such as infection, bacteremia, sepsis, severe sepsis, septic shock and the like.

The profile of biomarkers obtained from an individual, i.e., the test biomarker profile, is compared to a reference biomarker profile. The reference biomarker profile can be generated from one individual or a population of two or more individuals. The population, for example, may comprise three, four, five, ten, 15, 20, 30, 40, 50 or more individuals. Furthermore, the reference biomarker profile and the individual's (test) biomarker profile that are compared in the methods of the present invention may be generated from the same individual, provided that the test and reference profiles are generated from biological samples taken at different time points and compared to one another. For example, a sample may be obtained from an individual at the start of a study period. A reference biomarker profile taken from that sample may then be compared to biomarker profiles generated from subsequent samples from the same individual. Such a comparison may be used, for example, to determine the status of sepsis in the individual by repeated classifications over time.

The reference populations may be chosen from individuals who do not have SIRS ("SIRS-negative"), from individuals who do not have SIRS but who are suffering from an infectious process, from individuals who are suffering from SIRS without the presence of sepsis ("SIRS-positive"), from individuals who are suffering from the onset of sepsis, from individuals who are sepsis-positive and suffering from one of the stages in the progression of sepsis, or from individuals with a physiological trauma that increases the risk of developing sepsis. Furthermore, the reference populations may be SIRS-positive and are then subsequently diagnosed with sepsis using conventional techniques. For example, a population of SIRS-positive patients used to generate the reference profile may be diagnosed with sepsis about 24, 48, 72, 96 or more hours after biological samples were taken from them for the purposes of generating a reference profile. In one embodiment, the population of SIRS-positive individuals is diagnosed with sepsis using conventional techniques about 0-36 hours, about 36-60 hours, about 60-84 hours, or about 84-108 hours after the biological samples were taken. If the biomarker profile is indicative of sepsis or one of its stages of progression, a clinician may begin treatment prior to the manifestation of clinical symptoms of sepsis. Treatment typically will involve examining the patient to determine the source of the infection. Once locating the source, the clinician typically will obtain cultures from the site of the infection, preferably before beginning relevant empirical antimicrobial therapy and perhaps additional adjunctive therapeutic measures, such as draining an abscess or removing an infected catheter. Therapies for sepsis are reviewed in Healy, supra.

The methods of the present invention comprise comparing an individual's biomarker profile with a reference biomarker profile. As used herein, "comparison" includes any means to discern at least one difference in the individual's and the reference biomarker profiles. Thus, a comparison may include a visual inspection of chromatographic spectra, and a comparison may include arithmetical or statistical comparisons of values assigned to the features of the profiles. Such statistical comparisons include, but are not limited to, applying a decision rule. If the biomarker profiles comprise at least one internal standard, the comparison to discern a difference in the biomarker profiles may also include features of these internal standards, such that features of the biomarker are correlated to features of the internal standards. The comparison can predict, inter alia, the chances of acquiring sepsis or SIRS; or the comparison can confirm the presence or absence of sepsis or SIRS; or the comparison can indicate the stage of sepsis at which an individual may be.

The present invention, therefore, obviates the need to conduct time-intensive assays over a monitoring period, as well as the need to identify each biomarker. Although the invention does not require a monitoring period to classify an individual, it will be understood that repeated classifications of the individual, i.e., repeated snapshots, may be taken over time until the individual is no longer at risk. Alternatively, a profile of biomarkers obtained from the individual may be compared to one or more profiles of biomarkers obtained from the same individual at different points in time. The artisan will appreciate that each comparison made in the process of repeated classifications is capable of classifying the individual as having membership in the reference population.

Individuals having a variety of physiological conditions corresponding to the various stages in the progression of sepsis, from the absence of sepsis to MOD, may be distinguished by a characteristic biomarker profile. As used herein, an "individual" is an animal, preferably a mammal, more preferably a human or non-human primate. The terms "individual," "subject" and "patient" are used interchangeably herein. The individual can be normal, suspected of having SIRS or sepsis, at risk of developing SIRS or sepsis, or confirmed as having SIRS or sepsis. While there are many known biomarkers that have been implicated in the progression of sepsis, not all of these markers appear in the initial, pre-clinical stages. The subset of biomarkers characteristic of early-stage sepsis may, in fact, be determined only by a retrospective analysis of samples obtained from individuals who ultimately manifest clinical symptoms of sepsis. Without being bound by theory, even an initial pathologic infection that results in sepsis may provoke physiological changes that are reflected in particular changes in biomarker expression. Once the characteristic biomarker profile of a stage of sepsis, for example, is determined, the profile of biomarkers from a biological sample obtained from an individual may be compared to this reference profile to determine whether the test subject is also at that particular stage of sepsis.

The progression of a population from one stage of sepsis to another, or from normalcy (i.e., a condition characterized by not having sepsis or SIRS) to sepsis or SIRS and vice versa, will be characterized by changes in biomarker profiles, as certain biomarkers are expressed at increasingly higher levels and the expression of other biomarkers becomes down-regulated. These changes in biomarker profiles may reflect the progressive establishment of a physiological response in the reference population to infection and/or inflammation, for example. The skilled artisan will appreciate that the biomarker profile of the reference population also will change as a physiological response subsides. As stated above, one of the advantages of the present invention is the capability of classifying an individual with a biomarker profile from a single biological sample as having membership in a particular population. The artisan will appreciate, however, that the determination of whether a particular physiological response is becoming established or is subsiding may be facilitated by a subsequent classification of the individual. To this end, the present invention provides numerous biomarkers that both increase and decrease in level of expression as a physiological response to sepsis or SIRS is established or subsides. For example, an investigator can select a feature of an individual's biomarker profile that is known to change in intensity as a physiological response to sepsis becomes established. A comparison of the same feature in a profile from a subsequent biological sample from the individual can establish whether the individual is progressing toward more severe sepsis or is progressing toward normalcy.

The molecular identity of biomarkers is not essential to the invention. Indeed, the present invention should not be limited to biomarkers that have previously been identified. (See, e.g., U.S. patent application Ser. No. 10/400,275, filed Mar. 26, 2003.) It is, therefore, expected that novel biomarkers will be identified that are characteristic of a given population of individuals, especially a population in one of the early stages of sepsis. In one embodiment of the present invention, a biomarker is identified and isolated. It then may be used to raise a specifically-binding antibody, which can facilitate biomarker detection in a variety of diagnostic assays. For this purpose, any immunoassay may use any antibodies, antibody fragment or derivative capable of binding the biomarker molecules (e.g., Fab, Fv, or scFv fragments). Such immunoassays are well-known in the art. If the biomarker is a protein, it may be sequenced and its encoding gene may be cloned using well-established techniques.

The methods of the present invention may be employed to screen, for example, patients admitted to an ICU. A biological sample such as, for example, blood, is taken immediately upon admission. The complex mixture of proteins and other molecules within the blood is resolved as a profile of biomarkers. This may be accomplished through the use of any technique or combination of techniques that reproducibly distinguishes these molecules on the basis of some physical or chemical property. In one embodiment, the molecules are immobilized on a matrix and then are separated and distinguished by laser desorption/ionization time-of-flight mass spectrometry. A spectrum is created by the characteristic desorption pattern that reflects the mass/charge ratio of each molecule or its fragments. In another embodiment, biomarkers are selected from the various mRNA species obtained from a cellular extract, and a profile is obtained by hybridizing the individual's mRNA species to an array of cDNAs. The diagnostic use of cDNA arrays is well known in the art. (See, e.g., Zou, et. al., *Oncogene* 21: 4855-4862 (2002).) In yet another embodiment, a profile may be obtained using a combination of protein and nucleic acid separation methods.

The invention also provides kits that are useful in determining the status of sepsis or diagnosing SIRS in an individual. The kits of the present invention comprise at least one biomarker. Specific biomarkers that are useful in the present invention are set forth herein. The biomarkers of the kit can be used to generate biomarker profiles according to the present invention. Examples of classes of compounds of the kit include, but are not limited to, proteins, and fragments thereof, peptides, polypeptides, proteoglycans, glycoproteins, lipoproteins, carbohydrates, lipids, nucleic acids, organic and inorganic chemicals, and natural and synthetic polymers. The biomarker(s) may be part of an array, or the biomarker(s) may be packaged separately and/or individually. The kit may also comprise at least one internal standard to be used in generating the biomarker profiles of the present invention. Likewise, the internal standards can be any of the classes of compounds described above. The kits of the present invention also may contain reagents that can be used to detectably label biomarkers contained in the biological samples from which the biomarker profiles are generated. For this purpose, the kit may comprise a set of antibodies or functional fragments thereof that specifically bind at least two, three, four, five, 10, 20 or more of the biomarkers set forth in any one of the following TABLES that list biomarkers. The antibodies themselves may be detectably labeled. The kit also may comprise a specific biomarker binding component, such as an aptamer. If the biomarkers comprise a nucleic acid, the kit may provide an oligonucleotide probe that is capable of forming a duplex with the biomarker or with a complementary strand of a biomarker. The oligonucleotide probe may be detectably labeled.

The kits of the present invention may also include pharmaceutical excipients, diluents and/or adjuvants when the biomarker is to be used to raise an antibody. Examples of pharmaceutical adjuvants include, but are not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of an injectable pharmaceutical form can be brought about by the inclusion of agents which delay absorption such as aluminum monostearate and gelatin.

Generation of Biomarker Profiles

According to one embodiment, the methods of the present invention comprise obtaining a profile of biomarkers from a biological sample taken from an individual. The biological sample may be blood, plasma, serum, saliva, sputum, urine, cerebral spinal fluid, cells, a cellular extract, a tissue sample, a tissue biopsy, a stool sample and the like. The reference biomarker profile may be obtained, for example, from a population of individuals selected from the group consisting of SIRS-negative individuals, SIRS-positive individuals, individuals who are suffering from the onset of sepsis and individuals who already have sepsis. The reference biomarker profile from individuals who already have sepsis may be obtained at any stage in the progression of sepsis, such as infection, bacteremia, severe sepsis, septic shock or MOD.

In one embodiment, a separation method may be used to create a profile of biomarkers, such that only a subset of biomarkers within the sample is analyzed. For example, the biomarkers that are analyzed in a sample may consist of mRNA species from a cellular extract, which has been fractionated to obtain only the nucleic acid biomarkers within the sample, or the biomarkers may consist of a fraction of the total complement of proteins within the sample, which have been fractionated by chromatographic techniques. Alternatively, a profile of biomarkers may be created without employing a separation method. For example, a biological sample may be interrogated with a labeled compound that forms a specific complex with a biomarker in the sample, where the intensity of the label in the specific complex is a measurable characteristic of the biomarker. A suitable compound for forming such a specific complex is a labeled antibody. In one embodiment, a biomarker is measured using an antibody with an amplifiable nucleic acid as a label. In yet another embodiment, the nucleic acid label becomes amplifiable when two antibodies, each conjugated to one strand of a nucleic acid label, interact with the biomarker, such that the two nucleic acid strands form an amplifiable nucleic acid.

In another embodiment, the biomarker profile may be derived from an assay, such as an array, of nucleic acids, where the biomarkers are the nucleic acids or complements thereof. For example, the biomarkers may be ribonucleic acids. The biomarker profile also may be obtained using a method selected from the group consisting of nuclear magnetic resonance, nucleic acid arrays, dot blotting, slot blotting, reverse transcription amplification and Northern analysis. In another embodiment, the biomarker profile is detected immunologically by reacting antibodies, or functional fragments thereof, specific to the biomarkers. A functional fragment of an antibody is a portion of an antibody that retains at least some ability to bind to the antigen to which the complete antibody binds. The fragments, which include, but are not limited to, scFv fragments, Fab fragments and F(ab)$_2$ fragments, can be recombinantly produced or enzymatically produced. In another embodiment, specific binding molecules other than antibodies, such as aptamers, may be used to bind the biomarkers. In yet another embodiment, the biomarker profile may comprise a measurable aspect of an infectious agent or a component thereof. In yet another embodiment, the biomarker profile may comprise measurable aspects of small molecules, which may include fragments of proteins or nucleic acids, or which may include metabolites.

Biomarker profiles may be generated by the use of one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Other suitable separation methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

Biomarker profiles also may be generated by methods that do not require physical separation of the biomarkers themselves. For example, nuclear magnetic resonance (NMR) spectroscopy may be used to resolve a profile of biomarkers from a complex mixture of molecules. An analogous use of NMR to classify tumors is disclosed in Hagberg, *NMR Biomed.* 11: 148-56 (1998), for example. Additional procedures include nucleic acid amplification technologies, which may be used to generate a profile of biomarkers without physical separation of individual biomarkers. (See Stordeur et al., *J. Immunol. Methods* 259: 55-64 (2002) and Tan et al., *Proc. Nat'l Acad. Sci. USA* 99: 11387-11392 (2002), for example.)

In one embodiment, laser desorption/ionization time-of-flight mass spectrometry is used to create a profile of biomarkers where the biomarkers are proteins or protein fragments that have been ionized and vaporized off an immobilizing support by incident laser radiation. A profile is then created by the characteristic time-of-flight for each protein, which depends on its mass-to-charge ("m/z") ratio. A variety of laser desorption/ionization techniques are known in the art. (See, e.g., Guttman et al., *Anal. Chem.* 73: 1252-62 (2001) and Wei et al., *Nature* 399: 243-46 (1999).)

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 µL, with or without prior purification or fractionation. The lysates or sample can be concentrated or diluted prior to application onto the support surface. Laser desorption/ionization is then used to generate mass spectra of the sample, or samples, in as little as three hours.

In another embodiment, the total mRNA from a cellular extract of the individual is assayed, and the various mRNA species that are obtained from the biological sample are used as biomarkers. Profiles may be obtained, for example, by hybridizing these mRNAs to an array of probes, which may comprise oligonucleotides or cDNAs, using standard methods known in the art. Alternatively, the mRNAs may be subjected to gel electrophoresis or blotting methods such as dot blots, slot blots or Northern analysis, all of which are known in the art. (See, e.g., Sambrook et al. in "Molecular Cloning, 3rd ed.," Cold Spring Harbor Laboratory Press, Cold Spring Harbor, N.Y. (2001).) mRNA profiles also may be obtained by reverse transcription followed by amplification and detection of the resulting cDNAs, as disclosed by Stordeur et al., supra, for example. In another embodiment, the profile may be obtained by using a combination of methods, such as a nucleic acid array combined with mass spectroscopy.

Use of a Data Analysis Algorithm

In one embodiment, comparison of the individual's biomarker profile to a reference biomarker profile comprises applying a decision rule. The decision rule can comprise a data analysis algorithm, such as a computer pattern recognition algorithm. Other suitable algorithms include, but are not limited to, logistic regression or a nonparametric algorithm that detects differences in the distribution of feature values (e.g., a Wilcoxon Signed Rank Test). The decision rule may be based upon one, two, three, four, five, 10, 20 or more features. In one embodiment, the decision rule is based on hundreds or more of features. Applying the decision rule may also comprise using a classification tree algorithm. For example, the reference biomarker profile may comprise at least three features, where the features are predictors in a classification tree algorithm. The data analysis algorithm predicts membership within a population (or class) with an accuracy of at least about 60%, at least about 70%, at least about 80% and at least about 90%.

Suitable algorithms are known in the art, some of which are reviewed in Hastie et al., supra. Such algorithms classify complex spectra from biological materials, such as a blood sample, to distinguish individuals as normal or as possessing biomarker expression levels characteristic of a particular disease state. While such algorithms may be used to increase the speed and efficiency of the application of the decision rule and to avoid investigator bias, one of ordinary skill in the art will realize that computer-based algorithms are not required to carry out the methods of the present invention.

Algorithms may be applied to the comparison of biomarker profiles, regardless of the method that was used to generate the biomarker profile. For example, suitable algorithms can be applied to biomarker profiles generated using gas chromatography, as discussed in Harper, "Pyrolysis and GC in Polymer Analysis," Dekker, N.Y. (1985). Further, Wagner et al., *Anal. Chem.* 74: 1824-35 (2002) disclose an algorithm that improves the ability to classify individuals based on spectra obtained by static time-of-flight secondary ion mass spectrometry (TOF-SIMS). Additionally, Bright et al, *J. Microbiol. Methods* 48: 127-38 (2002) disclose a method of distinguishing between bacterial strains with high certainty (79-89% correct classification rates) by analysis of MALDI-TOF-MS spectra. Dalluge, *Fresenius J. Anal. Chem.* 366: 701-11 (2000) discusses the use of MALDI-TOF-MS and liquid chromatography-electrospray ionization mass spectrometry (LC/ESI-MS) to classify profiles of biomarkers in complex biological samples.

Biomarkers

J The methods of the present invention can be carried out by generation of a biomarker profile that is diagnostic or predictive of sepsis or SIRS. Because profile generation is sufficient to carry out the invention, the biomarkers that constitute the profile need not be known or subsequently identified.

Biomarkers that can be used to generate the biomarker profiles of the present invention may include those known to be informative of the state of the immune system in response to infection; however, not all of these biomarkers may be equally informative. These biomarkers can include hormones, autoantibodies, soluble and insoluble receptors, growth factors, transcription factors, cell surface markers and soluble markers from the host or from the pathogen itself, such as coat proteins, lipopolysaccharides (endotoxin), lipoteichoic acids, etc. Other biomarkers include, but are not limited to, cell-surface proteins such as CD64 proteins; CD11b proteins; HLA Class II molecules, including HLA-DR proteins and HLA-DQ proteins; CD54 proteins; CD71 proteins; CD86 proteins; surface-bound tumor necrosis factor receptor (TNF-R); pattern-recognition receptors such as Toll-like receptors; soluble markers such as interleukins IL-1, IL-2, IL-4, IL-6, IL-8, IL-10, IL-11, IL-12, IL-13, and IL-18; tumor necrosis factor alpha (TNF-α); neopterin; C-reactive protein (CRP); procalcitonin (PCT); 6-keto Flα; thromboxane $B_2$; leukotrienes B4, C3, C4, C5, D4 and E4; interferon gamma (IFNγ); interferon alpha/beta (IFN α/β); lymphotoxin alpha (LTα); complement components (C'); platelet activating factor (PAF); bradykinin; nitric oxide (NO); granulocyte macrophage-colony stimulating factor (GM-CSF); macrophage inhibitory factor (MIF); interleukin-1 receptor antagonist (IL-1ra); soluble tumor necrosis factor receptor (sTNFr); soluble interleukin receptors sIL-1r and sIL-2r; transforming growth factor beta (TGFβ); prostaglandin $E_2$ ($PGE_2$); granulocyte-colony stimulating factor (G-CSF); and other inflammatory mediators. (Reviewed in Oberholzer et al., *Shock* 16: 83-96 (2001) and Vincent et al. in "The Sepsis Text," Carlet et al., eds. (Kluwer Academic Publishers, 2002). Biomarkers commonly and clinically associated with bacteremia are also candidates for biomarkers useful for the present invention, given the common and frequent occurrence of such biomarkers in biological samples. Biomarkers can include low molecular weight compounds, which can be fragments of proteins or nucleic acids, or they may include metabolites. The presence or concentration of the low molecular weight compounds, such as metabolites, may reflect a phenotypic change that is associated with sepsis and/or SIRS. In particular, changes in the concentration of small molecule biomarkers may be associated with changes in cellular metabolism that result from any of the physiological changes in response to SIRS and/or sepsis, such as hypothermia or hyperthermia, increased heart rate or rate of respiration, tissue hypoxia, metabolic acidosis or MOD. Biomarkers may also include RNA and DNA molecules that encode protein biomarkers.

Biomarkers can also include at least one molecule involved in leukocyte modulation, such as neutrophil activation or monocyte deactivation. Increased expression of CD64 and CD11b is recognized as a sign of neutrophil and monocyte activation. (Reviewed in Oberholzer et al., supra and Vincent et al., supra.) Among those biomarkers that can be useful in the present invention are those that are associated with macrophage lysis products, as well as markers of changes in cytokine metabolism. (See Gagnon et al., *Cell* 110: 119-31 (2002); Oberholzer, et. al., supra; Vincent, et. al., supra.)

Biomarkers can also include signaling factors known to be involved or discovered to be involved in the inflammatory process. Signaling factors may initiate an intracellular cascade of events, including receptor binding, receptor activation, activation of intracellular kinases, activation of transcription factors, changes in the level of gene transcription and/or translation, and changes in metabolic processes, etc. The signaling molecules and the processes activated by these molecules collectively are defined for the purposes of the present invention as "biomolecules involved in the sepsis pathway." The relevant predictive biomarkers can include biomolecules involved in the sepsis pathway.

Accordingly, while the methods of the present invention may use an unbiased approach to identifying predictive biomarkers, it will be clear to the artisan that specific groups of biomarkers associated with physiological responses or with various signaling pathways may be the subject of particular attention. This is particularly the case where biomarkers from a biological sample are contacted with an array that can be used to measure the amount of various biomarkers through direct and specific interaction with the biomarkers (e.g., an antibody array or a nucleic acid array). In this case, the choice of the components of the array may be based on a suggestion that a particular pathway is relevant to the determination of the status of sepsis or SIRS in an individual. The indication that a particular biomolecule has a feature that is predictive or diagnostic of sepsis or SIRS may give rise to an expectation that other biomolecules that are physiologically regulated in a concerted fashion likewise may provide a predictive or diagnostic feature. The artisan will appreciate, however, that such an expectation may not be realized because of the complexity of biological systems. For example, if the amount of a specific mRNA biomarker were a predictive feature, a concerted change in mRNA expression of another biomarker might not be measurable, if the expression of the other biomarker was regulated at a post-translational level. Further, the mRNA expression level of a biomarker may be affected by multiple converging pathways that may or may not be involved in a physiological response to sepsis.

Biomarkers can be obtained from any biological sample, which can be, by way of example and not of limitation, blood, plasma, saliva, serum, urine, cerebral spinal fluid, sputum, stool, cells and cellular extracts, or other biological fluid sample, tissue sample or tissue biopsy from a host or patient. The precise biological sample that is taken from the individual may vary, but the sampling preferably is minimally invasive and is easily performed by conventional techniques.

Measurement of a phenotypic change may be carried out by any conventional technique. Measurement of body temperature, respiration rate, pulse, blood pressure, or other physiological parameters can be achieved via clinical observation and measurement. Measurements of biomarker molecules may include, for example, measurements that indicate the presence, concentration, expression level, or any other value associated with a biomarker molecule. The form of detection of biomarker molecules typically depends on the method used to form a profile of these biomarkers from a biological sample. For instance, biomarkers separated by 2D-PAGE are detected by Coomassie Blue staining or by silver staining, which are well-established in the art.

Isolation of Useful Biomarkers

It is expected that useful biomarkers will include biomarkers that have not yet been identified or associated with a relevant physiological state. In one aspect of the invention, useful biomarkers are identified as components of a biomarker profile from a biological sample. Such an identification may be made by any well-known procedure in the art, including immunoassay or automated microsequencing.

Once a useful biomarker has been identified, the biomarker may be isolated by one of many well-known isolation procedures. The invention accordingly provides a method of isolating a biomarker that is diagnostic or predictive of sepsis comprising obtaining a reference biomarker profile obtained from a population of individuals, identifying a feature of the reference biomarker profile that is predictive or diagnostic of sepsis or one of the stages in the progression of sepsis, identifying a biomarker that corresponds with that feature, and isolating the biomarker. Once isolated, the biomarker may be used to raise antibodies that bind the biomarker if it is a protein, or it may be used to develop a specific oligonucleotide probe, if it is a nucleic acid, for example.

The skilled artisan will readily appreciate that useful features can be further characterized to determine the molecular structure of the biomarker. Methods for characterizing biomolecules in this fashion are well-known in the art and include high-resolution mass spectrometry, infrared spectrometry, ultraviolet spectrometry and nuclear magnetic resonance. Methods for determining the nucleotide sequence of nucleic acid biomarkers, the amino acid sequence of polypeptide biomarkers, and the composition and sequence of carbohydrate biomarkers also are well-known in the art.

Application of the Present Invention to SIRS Patients

In one embodiment, the presently described methods are used to screen SIRS patients who are particularly at risk for developing sepsis. A biological sample is taken from a SIRS-positive patient, and a profile of biomarkers in the sample is compared to a reference profile from SIRS-positive individuals who eventually progressed to sepsis. Classification of the patient's biomarker profile as corresponding to the reference profile of a SIRS-positive population that progressed to sepsis is diagnostic that the SIRS-positive patient will likewise progress to sepsis. A treatment regimen may then be initiated to forestall or prevent the progression of sepsis.

In another embodiment, the presently described methods are used to confirm a clinical suspicion that a patient has SIRS. In this case, a profile of biomarkers in a sample is compared to reference populations of individuals who have SIRS or who do not have SIRS. Classification of the patient's biomarker profile as corresponding to one population or the other then can be used to diagnose the individual as having SIRS or not having SIRS.

EXAMPLES

The following examples are representative of the embodiments encompassed by the present invention and in no way limit the subject embraced by the present invention.

Example 1

Identification of Small Molecule Biomarkers Using Quantitative Liquid Chromatography/Electrospray Ionization Mass Spectrometry (LC/ESI-MS)

1.1. Samples Received and Analyzed

Reference biomarker profiles were established for two populations of patients. The first population ("the SIRS group") represented 20 patients who developed SIRS and who entered into the present study at "Day 1," but who did not progress to sepsis during their hospital stay. The second population ("the sepsis group") represented 20 patients who likewise developed SIRS and entered into the present study at Day 1, but who progressed to sepsis at least several days after entering the study. Blood samples were taken approximately every 24 hours from each study group. Clinical suspicion of sepsis in the sepsis group occurred at "time 0," as measured by conventional techniques. "Time—24 hours" and "time—48 hours" represent samples taken about 24 hours and about 48 hours, respectively, preceding the clinical suspicion of the onset of sepsis in the sepsis group. That is, the samples from the sepsis group included those taken on the day of entry into the study (Day 1), about 48 hours prior to clinical suspicion of sepsis (time—48 hours), about 24 hours prior to clinical suspicion of sepsis (time—24 hours), and on the day of clinical suspicion of the onset of sepsis (time 0). In total, 160 blood samples were analyzed: 80 samples from the 20 patients in the sepsis group and 80 samples from the 20 patients in the SIRS group.

1.2. Sample Preparation

In plasma, a significant number of small molecules may be bound to proteins, which may reduce the number of small molecules that are detected by a pattern-generating method. Accordingly, most of the protein was removed from the plasma samples following the release of small molecules that may be bound to the proteins. Appropriate methods to remove proteins include, but are not limited to, extraction of the plasma with ice-cold methanol, acetonitrile (ACN), butanol, or trichloroacetic acid (TCA), or heat denaturation and acid hydrolysis. In this example, plasma was extracted with ice-cold methanol. Methanol extraction was preferred because it resulted in the detection of the highest number of small molecules. 50 µL from each plasma sample were mixed with 100 µL ice-cold 100% methanol, giving a final volume percent of methanol of 67%. The solution was vortexed for 60 seconds. The samples were then incubated at 4° C. for 20 minutes, and proteins were precipitated by centrifugation at 12,000 rpm for 10 minutes. The supernatant was removed, dried, and resuspended in 50 µL water. Prior to LC/MS analysis, two low molecular weight molecules, sulfachloropyridazine and octadecylamine, were added to the extracted plasma samples. These molecules served as internal standards to normalize ion intensities and retention times. Sulfachloropyridazine has a m/z of 285.0 Da, determined by MS, and elutes at 44% ACN, determined by LC; octadecylamine has a m/z of 270.3 Da and elutes at 89% ACN.

1.3. LC/ESI-MS Analysis

10 µL of the resuspended supernatant was injected onto a 2.1×100 mm $C_{18}$ Waters Symmetry LC column (particle size=3.5 µm; interior bore diameter=100 Å). The column was then eluted at 300 µL/minute at a temperature of 25° C. with a three-step linear gradient of ACN in 0.1% formic acid. For t=0-0.5 minutes, the ACN concentration was 9.75% to 24%; for t=0.5-20 minutes, the ACN concentration was 24% to 90.5%; and for t=20-27 minutes, the ACN concentration was 90.5% to 92.4%. The aforementioned experimental conditions are herein referred to as "LC experimental conditions." Under LC experimental conditions, sulfachloropyridazine eluted at 44% ACN with a retention time of 6.4 minutes, and octadecylamine eluted at 89% ACN with a retention time of 14.5 minutes. Samples that were fractionated by LC were then subjected to ESI-MS using an Agilent MSD 1100 quadrupole mass spectrometer that was connected in tandem to the LC column (LC/ESI-MS). Mass spectral data were acquired for ions with a mass/charge ratio (m/z) ranging from 100 or 150-1000 Da in positive ion mode with a capillary voltage of 4000 V. The LC/ESI-MS analyses were performed three times for each sample. The data may be expressed as the m/z in Daltons and retention time in minutes (as "m/z, retention time") of each ion, where the retention time of an ion is the time required for elution from a reverse phase column in a linear ACN gradient. To account for slight variations in the retention time for run to run, however, the data also may be represented as the m/z and the percentage of ACN at which the ion elutes from a $C_{18}$ column, which represent inherent properties of the ions that will not be affected greatly by experimental variability. The relationship between retention time and the percent ACN at elution is expressed by the following equations:

| | |
|---|---|
| % ACN = 28.5 t + 9.75 | for 0 < t < 0.5; |
| % ACN = 3.4103 (t − 0.5) + 24 | for 0.5 < t < 20; and |
| % ACN = 0.27143 (t − 20) + 90.5 | for 20 < t < 27. |

The values for these parameters nevertheless should be understood to be approximations and may vary slightly between experiments; however, ions can be recognized reproducibly, especially if the samples are prepared with one or more internal standards. In the data shown below, the m/z values were determined to within ±0.4 m/z, while the percent ACN at which the ions elute is determined to within ±10%.

1.4. Data Analysis and Results

Several hundred spectral features were analyzed from each plasma sample. Similar features were aligned between spectra. The choice of alignment algorithm is not crucial to the present invention, and the skilled artisan is aware of various alignment algorithms that can be used for this purpose. In total, 4930 spectral features were analyzed. For the purpose of this Example, a "feature" is used interchangeably with a "peak" that corresponds to a particular ion. Representative peaks from samples obtained from five different individuals are shown in TABLE 1. The first column lists in parentheses the m/z and percentage of ACN at elution for each ion, respectively. The remaining columns are normalized intensities of the corresponding ions from each patient, which were determined by normalizing the intensities to those of the two internal standards. Over 400 peaks had an average normalized intensity higher than 0.1.

TABLE 1 presence of representative ions in various patients

| Ion (m/z, % ACN) | Patient 1 | Patient 2 | Patient 3 | Patient 4 | Patient 5 |
|---|---|---|---|---|---|
| (293.2, 26.8) | 43.39 | 42.44 | 53.81 | 45.86 | 23.24 |
| (496.5, 39.0) | 37.43 | 39.88 | 33.74 | 36.32 | 31.81 |
| (520.5, 37.8) | 9.067 | 9.309 | 7.512 | 6.086 | 6.241 |
| (522.5, 37.8) | 8.568 | 8.601 | 7.234 | 5.520 | 5.228 |
| (524.5, 42.2) | 11.60 | 12.73 | 8.941 | 7.309 | 6.810 |
| (275.3, 32.0) | 6.966 | 7.000 | 8.911 | 5.896 | 5.590 |
| (544.5, 37.8) | 3.545 | 3.915 | 3.182 | 2.365 | 2.342 |
| (393.3, 26.4) | 1.517 | 2.092 | 2.418 | 2.439 | 2.498 |
| (132.3, 24.3) | 2.317 | 2.417 | 3.953 | 4.786 | 2.982 |
| (437.4, 27.4) | 1.769 | 1.997 | 2.418 | 2.706 | 2.166 |
| (518.5, 39.0) | 3.731 | 3.792 | 6.758 | 3.058 | 2.605 |
| (349.3, 25.6) | 1.249 | 1.663 | 1.910 | 1.806 | 1.660 |
| (203.2, 24.1) | 3.722 | 3.485 | 4.900 | 3.155 | 2.342 |
| (481.4, 27.7) | 1.570 | 1.259 | 1.987 | 2.246 | 1.612 |

Various approaches may be used to identify ions that inform a decision rule to distinguish between the SIRS and sepsis groups. In this Example, the methods chosen were (1) comparing average ion intensities between the two groups, and (2) creating classification trees using a data analysis algorithm.

1.4.1. Comparing Average Ion Intensities

Figure 3:
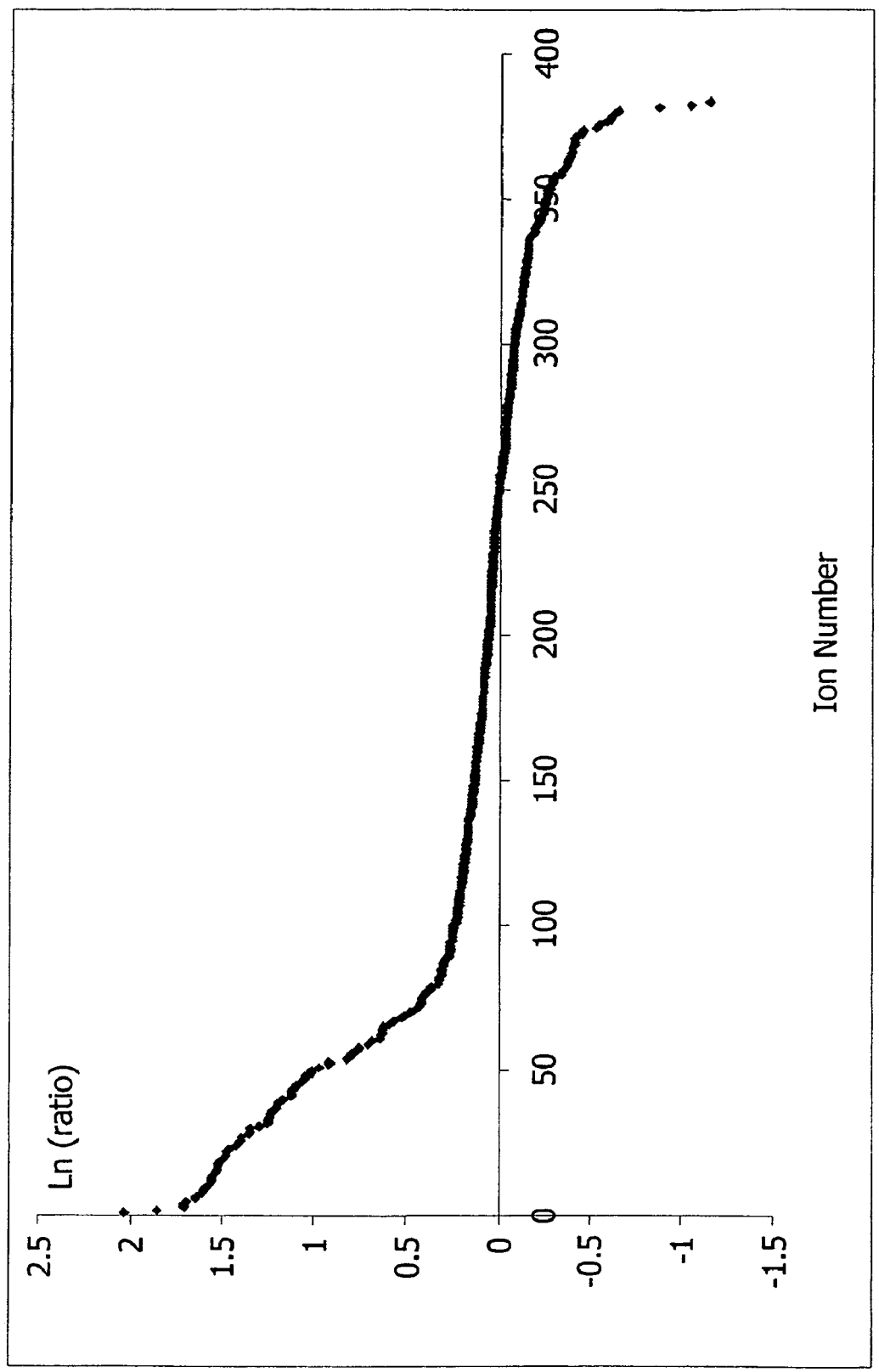
FIG. 3 shows the natural log of the ratio in average normalized peak intensities for about 400 ions for a sepsis-positive population versus a SIRS-positive population.

Comparison of averaged ion intensities effectively highlights differences in individual ion intensities between the SIRS and sepsis patients. Over 1800 normalized ion intensities were averaged separately for the sepsis group and the SIRS group. Ions having an average normalized intensity of less than 0.1 in either the sepsis group or the SIRS group were analyzed separately from those ions having a normalized intensity greater than 0.1 in profiles from both groups. The ratios of average normalized intensities for approximately 400 ions having a normalized intensity greater than 0.1 were determined for the sepsis group versus the SIRS group. A distribution of relative intensity ratios of these ions is shown in FIG. 3.

Using this method, 23 ions, listed in TABLE 2, were observed that displayed an intensity at least three-fold higher in samples from patients with sepsis than patients with SIRS (see FIG. 3, where the natural log of the ion intensity ratio is greater than about 1.1) and that were present in at least half of the patients with sepsis and generally in about a third or a quarter of the patients having SIRS. In this context, the "presence" of a biomarker means that the average normalized intensity of the biomarker in a particular patient was at least 25% of the normalized intensity averaged over all the patients. While these ions, or subsets thereof, will be useful for carrying out the methods of the present invention, additional ions or other sets of ions will be useful as well.

TABLE 2 percentage of patient samples containing the listed ion

| Ion # | (m/z [Da], retention time [min]) | % ACN at elution | Ion present in % of sepsis patients | Ion Present in % of SIRS patients |
|---|---|---|---|---|
| 1 | (520.4, 5.12) | 39.75 | 94 | 35 |
| 2 | (490.3, 5.12) | 39.75 | 76 | 35 |
| 3 | (407.2, 4.72) | 38.39 | 76 | 25 |
| 4 | (564.4, 5.28) | 40.30 | 71 | 35 |
| 5 | (608.4, 5.39) | 40.68 | 71 | 30 |
| 6 | (564.3, 2.14) | 29.59 | 71 | 25 |
| 7 | (476.4, 4.96) | 39.21 | 65 | 30 |
| 8 | (476.3, 1.86) | 28.64 | 65 | 35 |
| 9 | (377.2, 4.61) | 38.02 | 65 | 15 |
| 10 | (547.4, 5.28) | 40.30 | 65 | 20 |
| 11 | (657.4, 5.53) | 41.15 | 65 | 30 |
| 12 | (481.3, 4.96) | 39.21 | 59 | 25 |
| 13 | (432.3, 4.80) | 38.66 | 59 | 30 |
| 14 | (481.2, 1.86) | 28.64 | 59 | 20 |
| 15 | (388.3, 4.58) | 37.91 | 59 | 20 |
| 16 | (363.2, 4.40) | 37.30 | 59 | 20 |
| 17 | (261.2, 1.26) | 26.59 | 59 | 40 |
| 18 | (377.2, 9.32) | 54.08 | 59 | 15 |
| 19 | (534.3, 5.30) | 40.37 | 59 | 30 |
| 20 | (446.3, 4.94) | 39.14 | 59 | 25 |
| 21 | (437.2, 1.42) | 27.13 | 53 | 25 |
| 22 | (451.3, 4.94) | 39.14 | 53 | 15 |
| 23 | (652.5, 5.51) | 41.08 | 53 | 20 |

Subsets of these biomarkers were present in at least three-fold higher intensities in a majority of the sepsis-positive population. Specifically, at least 12 of these biomarkers were found at elevated levels in over half of the sepsis-positive population, and at least seven biomarkers were present in 85% of the sepsis-positive population, indicating that combinations of these markers will provide useful predictors of the onset of sepsis. All the biomarkers were at elevated levels with respect to the SIRS-positive population, as shown in TABLE 3.

TABLE 3 ion intensity in sepsis group versus SIRS group

| Ion | Intensity in sepsis group | Intensity in SIRS group | Ratio of intensities: sepsis/SIRS |
|---|---|---|---|
| (437.2, 1.42) | 4.13 | 0.77 | 5.36 |
| (520.4, 5.12) | 3.65 | 0.69 | 5.29 |
| (476.4, 4.96) | 3.34 | 0.78 | 3.56 |
| (481.3, 4.96) | 2.42 | 0.68 | 3.56 |
| (564.4, 5.28) | 2.39 | 0.43 | 5.56 |
| (432.3, 4.80) | 2.29 | 0.59 | 3.88 |

TABLE 3-continued ion intensity in sepsis group versus SIRS group

| Ion | Intensity in sepsis group | Intensity in SIRS group | Ratio of intensities: sepsis/SIRS |
|---|---|---|---|
| (476.3, 1.86) | 2.12 | 0.52 | 4.08 |
| (481.2, 1.86) | 1.88 | 0.42 | 4.48 |
| (388.3, 4.58) | 1.83 | 0.51 | 3.59 |
| (608.4, 5.39) | 1.41 | 0.24 | 5.88 |
| (363.2, 4.40) | 1.35 | 0.27 | 5.00 |
| (490.3, 5.12) | 1.27 | 0.25 | 5.08 |
| (261.2, 1.26) | 1.24 | 0.24 | 5.17 |
| (407.2, 4.72) | 1.05 | 0.17 | 6.18 |
| (377.2, 9.32) | 1.04 | 0.27 | 3.85 |
| (534.3, 5.30) | 0.88 | 0.16 | 5.50 |
| (446.3, 4.94) | 0.88 | 0.22 | 4.00 |
| (547.4, 5.28) | 0.86 | 0.16 | 5.38 |
| (451.3, 4.94) | 0.86 | 0.17 | 5.06 |
| (377.2, 4.61) | 0.84 | 0.22 | 3.82 |
| (564.3, 2.14) | 0.62 | 0.14 | 4.43 |
| (652.5, 5.51) | 0.62 | 0.10 | 6.20 |
| (657.4, 5.53) | 0.39 | 0.11 | 3.55 |

The two ions listed in TABLE 4 were observed to have an average normalized intensity three-fold higher in the SIRS population than in the sepsis population. (See FIG. 3, where the natural log of the ion intensity ratio is less than about −1.1.)

TABLE 4 ion intensity in sepsis group versus SIRS group

| Ion # | Intensity in sepsis group | Intensity in SIRS group | Ratio of intensities: sepsis/SIRS |
|---|---|---|---|
| (205.0, 0.01) | 0.26 | 0.81 | 0.32 |
| (205.2, 3.27) | 0.29 | 0.82 | 0.35 |

Thirty-two ions having an average normalized intensity of greater than 0.1 were identified that exhibited at least a three-fold higher intensity in the sepsis group versus the SIRS group. These ions are listed in TABLE 5A. Likewise, 48 ions having an average normalized intensity of less than 0.1 were identified that had a three-fold ratio of intensity higher in the sepsis group versus the SIRS group. These ions are listed in TABLE 5B. (A negative retention time reflects the fact that retention times are normalized against internal standards.)

TABLE 5A ions having an averaged normalized intensity > 0.1

| Ion | Intensity in sepsis group | Intensity in SIRS group | Ratio of intensities: sepsis/SIRS | Ln (ratio) |
|---|---|---|---|---|
| (365.2, 2.69) | 1.031828095 | 0.135995335 | 7.587231542 | 2.026467 |
| (305.2, 1.87) | 3.070957223 | 0.481494549 | 6.377968828 | 1.85285 |
| (407.2, 4.72) | 0.913022768 | 0.166525859 | 5.482768698 | 1.70161 |
| (459.1, 0.83) | 0.58484531 | 0.106723807 | 5.479989222 | 1.701103 |
| (652.5, 5.51) | 0.528195058 | 0.102545088 | 5.150856731 | 1.639163 |
| (608.4, 5.39) | 1.205608851 | 0.236066662 | 5.107069514 | 1.630626 |
| (415.3, 4.80) | 2.321268423 | 0.46651355 | 4.975779207 | 1.604582 |
| (319.0, 0.69) | 1.034850099 | 0.209420422 | 4.941495631 | 1.597668 |
| (534.3, 5.30) | 0.756349296 | 0.158850924 | 4.761378001 | 1.560537 |
| (564.4, 5.28) | 2.037002742 | 0.432651771 | 4.708180752 | 1.549302 |
| (437.2, 1.42) | 3.536425702 | 0.770241153 | 4.591322718 | 1.524168 |
| (520.4, 5.12) | 3.115934457 | 0.685511116 | 4.545417838 | 1.51412 |
| (261.2, 1.26) | 1.078475479 | 0.239640228 | 4.500394154 | 1.504165 |
| (363.2, 4.40) | 1.159043471 | 0.265797517 | 4.360625655 | 1.472616 |
| (451.3, 4.94) | 0.738875795 | 0.170611107 | 4.330760214 | 1.465743 |
| (490.3, 5.12) | 1.084054201 | 0.25339878 | 4.278056119 | 1.453499 |

TABLE 5A-continued ions having an averaged normalized intensity > 0.1

| Ion | Intensity in sepsis group | Intensity in SIRS group | Ratio of intensities: sepsis/SIRS | Ln (ratio) |
|---|---|---|---|---|
| (409.3, 2.79) | 1.172523824 | 0.281931606 | 4.158894565 | 1.425249 |
| (497.3, 4.98) | 0.409558491 | 0.100673382 | 4.068190437 | 1.403198 |
| (453.2, 2.97) | 0.738638127 | 0.184100346 | 4.012149581 | 1.389327 |
| (481.2, 1.86) | 1.609705934 | 0.418739646 | 3.844168924 | 1.346557 |
| (564.3, 2.14) | 0.531918507 | 0.139341563 | 3.817371482 | 1.339562 |
| (476.4, 4.96) | 2.847539378 | 0.784495859 | 3.629769802 | 1.289169 |
| (446.3, 4.94) | 0.752613738 | 0.216182996 | 3.481373426 | 1.247427 |
| (476.3, 1.86) | 1.811980008 | 0.521460142 | 3.474819762 | 1.245543 |
| (377.2, 4.61) | 0.75347133 | 0.217838186 | 3.458857892 | 1.240938 |
| (344.3, 4.21) | 0.560262239 | 0.164687938 | 3.401962791 | 1.224353 |
| (377.2, 9.32) | 0.902933137 | 0.267048623 | 3.381156311 | 1.218218 |
| (432.3, 4.80) | 1.957941965 | 0.588612075 | 3.326370706 | 1.201882 |
| (595.4, 6.36) | 0.41462875 | 0.125522805 | 3.303214496 | 1.194896 |
| (358.3, 4.40) | 0.351038883 | 0.106282278 | 3.302891964 | 1.194798 |
| (657.4, 5.53) | 0.336357992 | 0.105101129 | 3.200327108 | 1.163253 |
| (388.3, 4.58) | 1.561368263 | 0.510848809 | 3.056419503 | 1.117244 |

TABLE 5B ions having an averaged normalized intensity < 0.1

| Ion | Intensity in sepsis group | Intensity in SIRS group | Ratio of intensities: sepsis/SIRS | Ln (ratio) |
|---|---|---|---|---|
| (282.2, 0.91) | 0.16624 | 0.00024 | 693.08684 | 6.54116 |
| (289.2, 6.44) | 0.13088 | 0.00143 | 91.27187 | 4.51384 |
| (821.9, 2.49) | 0.13670 | 0.00996 | 13.72695 | 2.61936 |
| (385.3, 1.24) | 0.32177 | 0.03201 | 10.05211 | 2.30778 |
| (843.9, 2.47) | 0.11866 | 0.01206 | 9.83497 | 2.28594 |
| (407.2, 1.17) | 0.75611 | 0.08227 | 9.19041 | 2.21816 |
| (350.1, 0.86) | 0.10369 | 0.01174 | 8.83532 | 2.17876 |
| (385.3, 4.72) | 0.32430 | 0.03725 | 8.70689 | 2.16411 |
| (399.2, 2.99) | 0.15303 | 0.02091 | 7.31838 | 1.99039 |
| (152.1, 1.51) | 0.28888 | 0.04167 | 6.93310 | 1.93631 |
| (341.0, 0.36) | 0.26310 | 0.03828 | 6.87289 | 1.92759 |
| (451.2, 1.42) | 0.45398 | 0.06645 | 6.83232 | 1.92166 |
| (231.0, −0.41) | 0.19637 | 0.03362 | 5.84078 | 1.76486 |
| (534.2, 2.20) | 0.45796 | 0.08650 | 5.29427 | 1.66663 |
| (820.5, 7.02) | 0.12838 | 0.02439 | 5.26324 | 1.66075 |
| (578.4, 5.46) | 0.45661 | 0.08861 | 5.15298 | 1.63957 |
| (355.1, 2.85) | 0.16920 | 0.03334 | 5.07491 | 1.62431 |
| (358.0, 2.13) | 0.27655 | 0.05565 | 4.96946 | 1.60331 |
| (696.5, 5.65) | 0.20458 | 0.04223 | 4.84500 | 1.57795 |
| (622.4, 5.61) | 0.20034 | 0.04179 | 4.79410 | 1.56739 |
| (460.3, 4.02) | 0.18099 | 0.03950 | 4.58160 | 1.52205 |
| (718.0, 7.02) | 0.11733 | 0.02564 | 4.57688 | 1.52102 |
| (305.3, 6.11) | 0.10194 | 0.02324 | 4.38703 | 1.47865 |
| (283.2, 1.85) | 0.41312 | 0.09709 | 4.25497 | 1.44809 |
| (701.4, 5.63) | 0.18369 | 0.04321 | 4.25111 | 1.44718 |
| (541.2, 1.71) | 0.11482 | 0.02739 | 4.19217 | 1.43322 |
| (657.3, 2.49) | 0.17904 | 0.04280 | 4.18327 | 1.43109 |
| (239.2, 1.04) | 0.10637 | 0.02553 | 4.16574 | 1.42689 |
| (608.3, 2.35) | 0.39410 | 0.09670 | 4.07556 | 1.40501 |
| (465.0, 1.19) | 0.10817 | 0.02718 | 3.98030 | 1.38136 |
| (333.1, 2.00) | 0.35105 | 0.08919 | 3.93582 | 1.37012 |
| (497.3, 0.88) | 0.36172 | 0.09212 | 3.92666 | 1.36779 |
| (541.3, 5.12) | 0.13883 | 0.03559 | 3.90124 | 1.36129 |
| (627.3, 5.75) | 0.16498 | 0.04259 | 3.87347 | 1.35415 |
| (652.1, 5.87) | 0.17554 | 0.04558 | 3.85130 | 1.34841 |
| (402.2, 1.19) | 0.25423 | 0.06860 | 3.70596 | 1.30994 |
| (553.3, 5.38) | 0.16633 | 0.04578 | 3.63335 | 1.29016 |
| (635.4, 5.53) | 0.11925 | 0.03383 | 3.52512 | 1.25992 |
| (319.2, 6.34) | 0.17736 | 0.05035 | 3.52259 | 1.25920 |
| (231.1, 2.62) | 0.20535 | 0.05906 | 3.47671 | 1.24609 |
| (283.1, 4.96) | 0.17190 | 0.04984 | 3.44919 | 1.23814 |
| (766.0, 6.77) | 0.13671 | 0.04032 | 3.39069 | 1.22103 |
| (358.0, 6.00) | 0.20857 | 0.06194 | 3.36714 | 1.21406 |
| (179.0, 10.16) | 0.16841 | 0.05106 | 3.29838 | 1.19343 |
| (209.1, 10.98) | 0.13267 | 0.04090 | 3.24363 | 1.17669 |

TABLE 5B-continued ions having an averaged normalized intensity < 0.1

| Ion | Intensity in sepsis group | Intensity in SIRS group | Ratio of intensities: sepsis/SIRS | Ln (ratio) |
|---|---|---|---|---|
| (509.3, 5.28) | 0.26857 | 0.08291 | 3.23925 | 1.17534 |
| (337.2, 9.32) | 0.18169 | 0.05691 | 3.19236 | 1.16076 |
| (423.2, 2.88) | 0.16242 | 0.05097 | 3.18669 | 1.15898 |

Thus, the reference biomarker profiles of the invention may comprise a combination of features, where the features may be intensities of ions having a m/z of about 100 or 150 Da to about 1000 Da as determined by electrospray ionization mass spectrometry in the positive mode, and where the features have a ratio of average normalized intensities in a sepsis-positive reference population versus a SIRS-positive reference population of about 3:1 or higher. Alternatively, the features may have a ratio of average normalized intensities in a sepsis-positive reference population versus a SIRS-positive reference population of about 1:3 or lower. Because these biomarkers appear in biomarker profiles obtained from biological samples taken about 48 hours prior to the onset of sepsis, as determined by conventional techniques, they are expected to be predictors of the onset of sepsis.

1.4.2. Changes in Feature Intensity Over Time

The examined biomarker profiles displayed features that were expressed both at increasingly higher levels and at lower levels as individuals progressed toward the onset of sepsis. It is expected that the biomarkers corresponding to these features are characteristics of the physiological response to infection and/or inflammation in the individuals. For the reasons set forth above, it is expected that these biomarkers will provide particularly useful predictors for determining the status of sepsis or SIRS in an individual. Namely, comparisons of these features in profiles obtained from different biological samples from an individual are expected to establish whether an individual is progressing toward severe sepsis or whether SIRS is progressing toward normalcy.

Figure 4A:
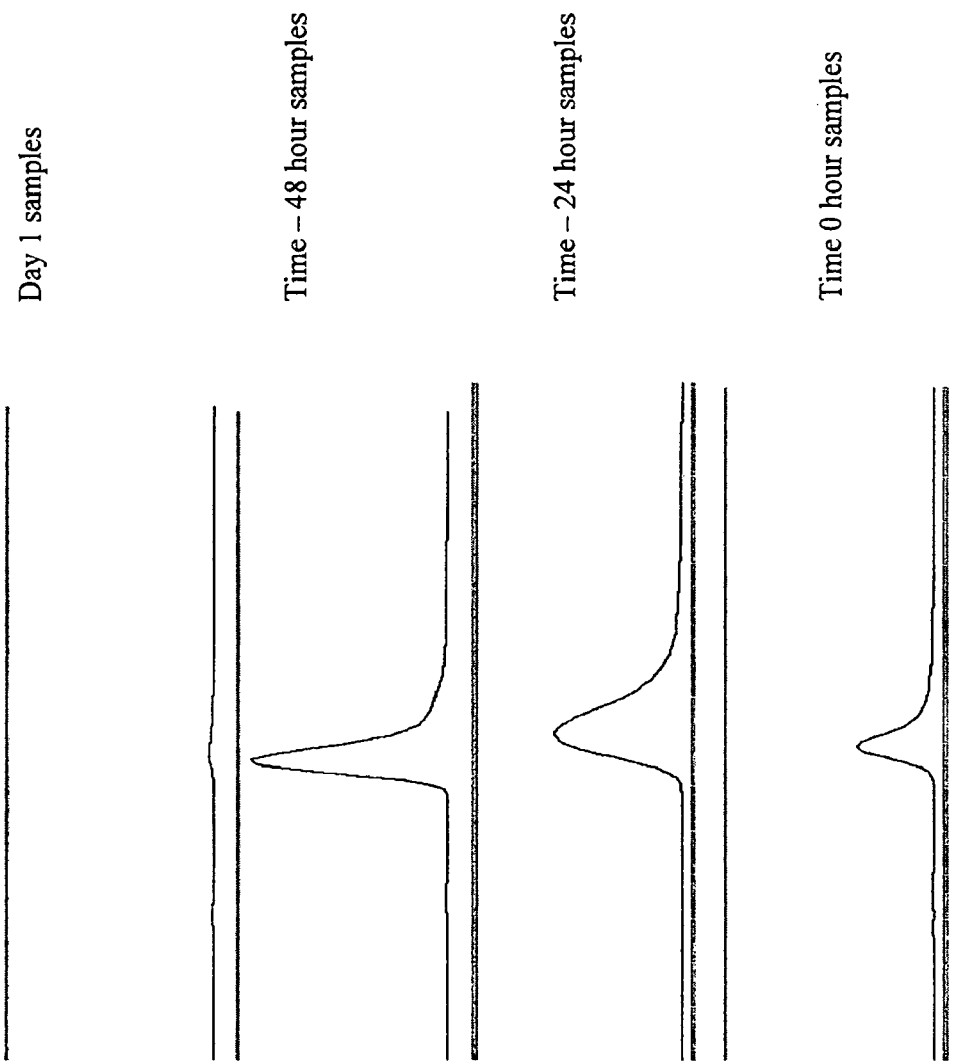
FIGS. 4A and 4B show the intensity of an ion having an m/z of 437.2 Da and a retention time on a $C_{18}$ reverse phase column of 1.42 min in an ESI-mass spectrometer profile.
Figure 4B:
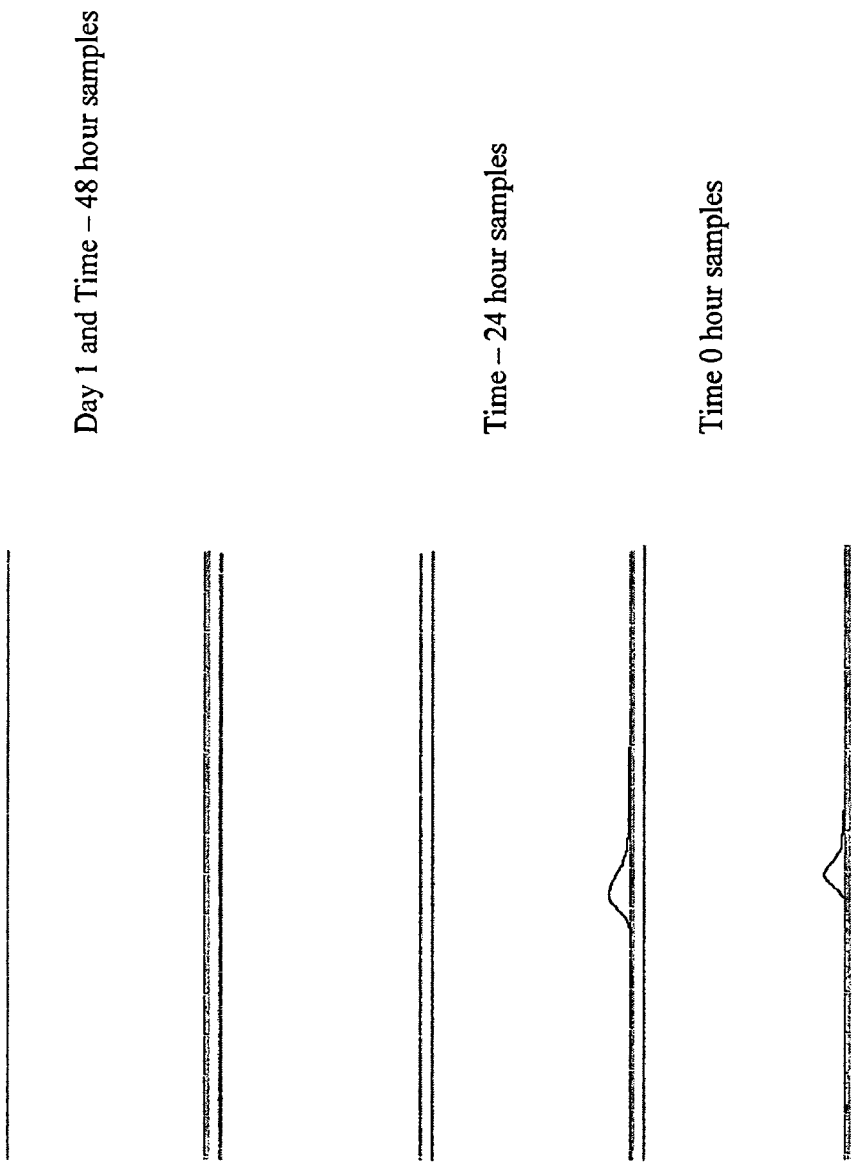

Of the 23 ions listed in TABLE 2, 14 showed a maximum intensity in the time—48 hours population, eight showed a maximum intensity in the time—24 hours population, and one showed a maximum intensity in the time 0 population. A representative change in the intensity of a biomarker over time in biological samples from the sepsis group is shown in FIG. 4A, while the change in the intensity of the same biomarker in biological samples from the SIRS group is shown in FIG. 4B. This particular ion, which has a m/z of 437.2 Da and a retention time of 1.42 min, peaks in intensity in the sepsis group 48 hours prior to the conversion of these patients to sepsis, as diagnosed by conventional techniques. A spike in relative intensity of this ion in a biological sample thus serves as a predictor of the onset of sepsis in the individual within about 48 hours.

1.4.3. Cross-Validation

A selection bias can affect the identification of features that inform a decision rule, when the decision rule is based on a large number of features from relatively few biomarker profiles. (See Ambroise et al., *Proc. Nat'l Acad. Sci. USA* 99: 6562-66 (2002).) Selection bias may occur when data are used to select features, and performance then is estimated conditioned on the selected features with no consideration made for the variability in the selection process. The result is an overestimation of the classification accuracy. Without compensation for selection bias, classification accuracies may reach 100%, even when the decision rule is based on random input parameters. (Id.) Selection bias may be avoided by including feature selection in the performance estimation process, whether that performance estimation process is 10-fold cross-validation or a type of bootstrap procedure. (See, e.g., Hastie et al., supra, at 7.10-7.11, herein incorporated by reference.)

In one embodiment of the present invention, model performance is measured by ten-fold cross-validation. Ten-fold cross-validation proceeds by randomly partitioning the data into ten exclusive groups. Each group in turn is excluded, and a model is fitted to the remaining nine groups. The fitted model is applied to the excluded group, and predicted class probabilities are generated. The predicted class probabilities can be compared to the actual class memberships by simply generating predicted classes. For example, if the probability of sepsis is, say, greater than 0.5, the predicted class is sepsis.

Deviance is a measure comparing probabilities with actual outcomes. As used herein, "deviance" is defined as:

$$-2\left\{\sum_{sepsis\ cases} \ln(P(sepsis)) + \sum_{SIRS\ cases} \ln(P(SIRS))\right\}$$

where P is the class probability for the specified class. Deviance is minimized when class probabilities are high for the actual classes. Two models can make the same predictions for given data, yet a preferred model would have a smaller predictive deviance. For each of the ten iterations in the ten-fold cross-validation, the predicted deviance is calculated for the cases left out of the model fitting during that iteration. The result is 10 unbiased deviances. Typically, these 10 deviances are summed to create a general summary of model performance (i.e., accuracy) on the total data set. Because in fact 10 different models were fit, cross-validation does not prove the performance of a specific model. Rather, the 10 models were generated by a common modeling process, and cross-validation proved the performance of this process. An eleventh model arising from this process will likely have predictive performance similar to those of the first 10. Use of a ten-fold cross-validation typically results in a model performance of less than 100%, but the performance obtained after ten-fold cross-validation is expected to reflect more closely a biologically meaningful predictive accuracy of the decision rule, when applied to biomarker profiles obtained from samples outside of the training set.

1.4.4. Classification Tree Analysis

One approach to analyze this data is to use a classification tree algorithm that searches for patterns and relationships in large datasets. A "classification tree" is a recursive partition to classify a particular patient into a specific class (e.g., sepsis or SIRS) using a series of questions that are designed to accurately place the patient into one of the classes. Each question asks whether a patient's condition satisfies a given predictor, with each answer being used to guide the user down the classification tree until a class into which the patient falls can be determined. As used herein, a "predictor" is the range of values of the features—in this Example, ion intensities—of one ion having a characteristic m/z and elution profile from a $C_{18}$ column in ACN. The "condition" is the single, specific value of the feature that is measured in the individual's biomarker profile. In this example, the "class names" are sepsis and SIRS. Thus, the classification tree user will first ask if a first ion intensity measured in the individual's biomarker profile falls within a given range of the first ion's predictive range.

The answer to the first question may be dispositive in determining if the individual has SIRS or sepsis. On the other hand, the answer to the first question may further direct the user to ask if a second ion intensity measured in the individual's biomarker profile falls within a given range of the second ion's predictive range. Again, the answer to the second question may be dispositive or may direct the user further down the classification tree until a patient classification is ultimately determined.

Figure 5:
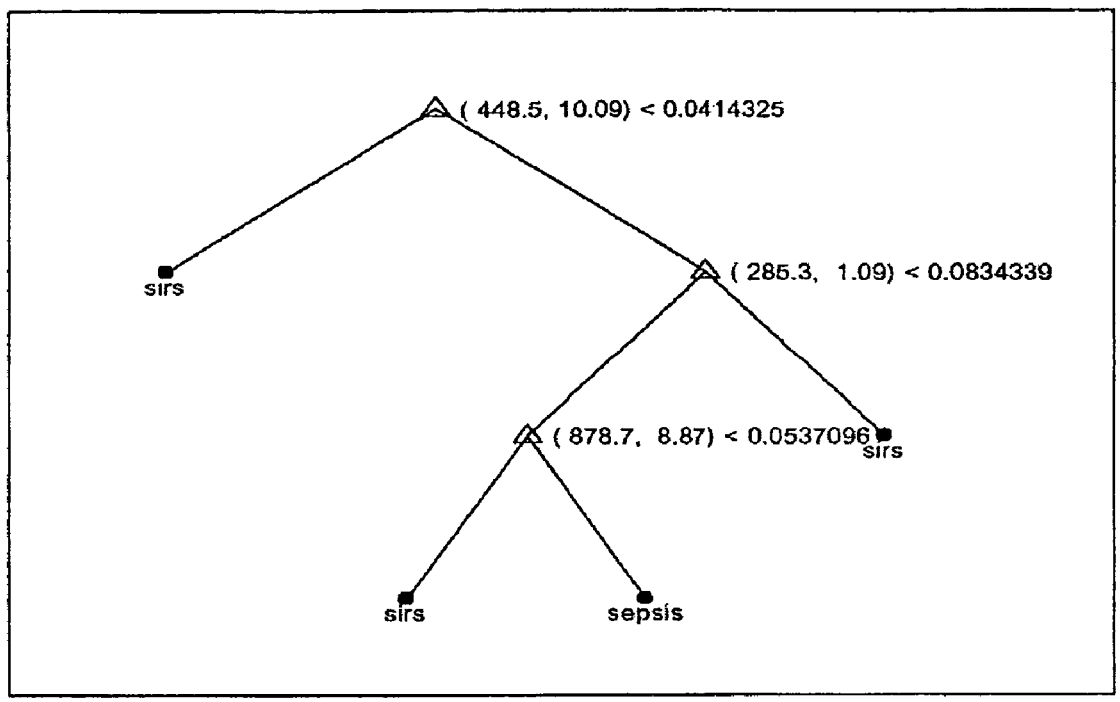
FIG. 5 is a classification tree fitted to data from time 0 in 10 sepsis patients and 10 SIRS patients, showing three biomarkers identified by electrospray mass spectrometry that are involved in distinguishing sepsis from SIRS.

A representative set of ion intensities collected from sepsis and SIRS populations at time 0 was analyzed with a classification tree algorithm, the results of which are shown in FIG. 5. In this case, the set of analyzed ions included those with normalized intensities of less than 0.1. The first decision point in the classification tree is whether the ion having a m/z of about 448.5 Daltons and a percent ACN at elution of about 32.4% has a normalized intensity of less than about 0.0414. If the answer to that question is "yes," then one proceeds down the left branch either to another question or to a class name. In this case, if the normalized intensity were less than about 0.0414, then one proceeds to the class name of "SIRS," and the individual is classified as SIRS-positive, but sepsis-negative. If the answer were "no," then one proceeds down the right branch to the next decision point, and so on until a class name is reached. In this example, three decision points were used to predict a class name for an individual. While a single decision point may be used to classify patients as SIRS- or sepsis-positive, additional decision points using other ions generally improved the accuracy of the classification. The skilled artisan will appreciate that many different classification trees are possible from large datasets. That is, there are many possible combinations of biomarkers that can be used to classify an individual as belonging to a SIRS population or a sepsis population, for example.

1.4.5. Multiple Additive Regression Trees

An automated, flexible modeling technique that uses multiple additive regression trees (MART) was used to classify sets of features as belonging to one of two populations. A MART model uses an initial offset, which specifies a constant that applies to all predictions, followed by a series of regression trees. Its fitting is specified by the number of decision points in each tree, the number of trees to fit, and a "granularity constant" that specifies how radically a particular tree can influence the MART model. For each iteration, a regression tree is fitted to estimate the direction of steepest descent of the fitting criterion. A step having a length specified by the granularity constant is taken in that direction. The MART model then consists of the initial offset plus the step provided by the regression tree. The differences between the observed and predicted values are recalculated, and the cycle proceeds again, leading to a progressive refinement of the prediction. The process continues either for a predetermined number of cycles or until some stopping rule is triggered.

The number of splits in each tree is a particularly meaningful fitting parameter. If each tree has only one split, the model looks only at one feature and has no capability for combining two predictors. If each tree has two splits, the model can accommodate two-way interactions among features. With three trees, the model can accommodate three-way interactions, and so forth.

The value of sets of features in predicting class status was determined for data sets with features and known class status (e.g., sepsis or SIRS). MART provides a measure of the contribution or importance of individual features to the classification decision rule. Specifically, the degree to which a single feature contributes to the decision rule upon its selection at a given tree split can be measured to provide a ranking of features by their importance in determining the final decision rule. Repeating the MART analysis on the same data set may yield a slightly different ranking of features, especially with respect to those features that are less important in establishing the decision rule. Sets of predictive features and their corresponding biomarkers that are useful for the present invention, therefore, may vary slightly from those set forth herein.

One implementation of the MART technology is found in a module, or "package," for the R statistical programming environment (see Venables et al., in *Modern Applied Statistics with S*, $4^{th}$ ed. (Springer, 2002); www.r-project.org). Results reported in this document were calculated using R versions 1.7.0 and 1.7.1. The module implementing MART, written by Dr. Greg Ridgeway, is called "gbm" and is also freely available for download (see www.r-project.org). The MART algorithm is amenable to ten-fold cross-validation. The granularity parameter was set to 0.05, and the gbm package's internal stopping rule was based on leaving out 20% of the data cases at each marked iteration. The degree of interaction was set to one, so no interactions among features were considered. The gbm package estimates the relative importance of each feature on a percentage basis, which cumulatively equals 100% for all the features of the biomarker profile. The features with highest importance, which together account for at least 90% of total importance, are reported as potentially having predictive value. Note that the stopping rule in the fitting of every MART model contributes a stochastic component to model fitting and feature selection. Consequently, multiple MART modeling runs based on the same data may choose slightly, or possibly even completely, different sets of features. Such different sets convey the same predictive information; therefore, all the sets are useful in the present invention. Fitting MART models a sufficient number of times is expected to produce all the possible sets of predictive features within a biomarker profile. Accordingly, the disclosed sets of predictors are merely representative of those sets of features that can be used to classify individuals into populations.

1.4.6. Logistic Regression Analysis

Logistic regression provides yet another means of analyzing a data stream from the LC/MS analysis described above. "Peak intensity" is measured by the height of a peak that appears in a spectrum at a given m/z location. The absence of a peak at a given m/z location results in an assigned peak intensity of "0." The standard deviations (SD) of the peak intensities from a given m/z location are then obtained from the spectra of the combined SIRS and sepsis populations. If there is no variation in peak intensity between SIRS and sepsis populations (i.e., the SD=0), the peak intensity is not considered further. Before regression analysis, peak intensities are scaled, using methods well-known in the art. Scaling algorithms are generally described in, Hastie et al., supra, at Chapter 11.

This feature-selection procedure identified 26 input parameters (i.e., biomarkers) from time 0 biomarker profiles, listed in TABLE 6. Although input parameter are ranked in order of statistical importance, lower ranked input parameters still may prove clinically valuable and useful for the present invention. Further, the artisan will understand that the ranked importance of a given input parameter may change if the reference population changes in any way.

TABLE 6 input parameters from time 0 samples

| Rank of input parameter importance | m/z (Da) | % ACN at elution |
|---|---|---|
| 1 | 883.6 | 44.84 |
| 2 | 718.1 | 44.94 |
| 3 | 957.3 | 44.84 |
| 4 | 676.1 | 44.84 |
| 5 | 766.0 | 44.77 |
| 6 | 416.3 | 40.10 |
| 7 | 429.4 | 75.80 |
| 8 | 820.6 | 44.84 |
| 9 | 399.4 | 90.43 |
| 10 | 244.2 | 26.59 |
| 11 | 593.5 | 43.51 |
| 12 | 300.4 | 59.54 |
| 13 | 285.3 | 25.88 |
| 14 | 377.0 | 25.26 |
| 15 | 194.1 | 27.07 |
| 16 | 413.4 | 92.04 |
| 17 | 651.5 | 59.98 |
| 18 | 114.2 | 34.40 |
| 19 | 607.5 | 45.21 |
| 20 | 282.3 | 37.30 |
| 21 | 156.2 | 39.99 |
| 22 | 127.3 | 64.68 |
| 23 | 687.9 | 41.84 |
| 24 | 439.5 | 43.34 |
| 25 | 462.4 | 72.70 |
| 26 | 450.4 | 64.79 |

Using this same logistic regression analysis, biomarkers can be ranked in order of importance in predicting the onset of sepsis using samples taken at time—48 hours. The feature-selection process yielded 37 input parameters for the time—48 hour samples as shown in TABLE 7.

TABLE 7 input parameters from time t-48 hours samples

| Rank of input parameter importance | m/z (Da) | % ACN at elution |
|---|---|---|
| 1 | 162.2 | 28.57 |
| 2 | 716.2 | 46.41 |
| 3 | 980 | 54.52 |
| 4 | 136.2 | 24.65 |
| 5 | 908.9 | 57.83 |
| 6 | 150.2 | 25.13 |
| 7 | 948.7 | 52.54 |
| 8 | 298.4 | 25.52 |
| 9 | 293.3 | 30.45 |
| 10 | 188.2 | 30.65 |
| 11 | 772.7 | 47.53 |
| 12 | 327.4 | 100.60 |
| 13 | 524.5 | 90.30 |
| 14 | 205.2 | 33.28 |
| 15 | 419.4 | 87.81 |
| 16 | 804.8 | 54.86 |
| 17 | 496.5 | 79.18 |
| 18 | 273.1 | 29.39 |
| 19 | 355.4 | 95.51 |
| 20 | 379.3 | 38.63 |
| 21 | 423.3 | 39.04 |
| 22 | 463.4 | 87.50 |
| 23 | 965.3 | 54.15 |
| 24 | 265.3 | 40.10 |
| 25 | 287.2 | 40.47 |
| 26 | 429.4 | 83.13 |
| 27 | 886.9 | 54.42 |
| 28 | 152.2 | 28.33 |
| 29 | 431.4 | 61.34 |

TABLE 7-continued input parameters from time t-48 hours samples

| Rank of input parameter importance | m/z (Da) | % ACN at elution |
|---|---|---|
| 30 | 335.4 | 30.72 |
| 31 | 239.2 | 43.75 |
| 32 | 373.4 | 61.10 |
| 33 | 771 | 24.03 |
| 34 | 555.4 | 41.43 |
| 35 | 116.2 | 24.95 |
| 36 | 887.2 | 54.62 |
| 37 | 511.4 | 40.95 |

1.4.7. Wilcoxon Signed Rank Test Analysis

In yet another method, a nonparametric test such as a Wilcoxon Signed Rank Test can be used to identify individual biomarkers of interest. The features in a biomarker profile are assigned a "p-value," which indicates the degree of certainty with which the biomarker can be used to classify individuals as belonging to a particular reference population. Generally, a p-value having predictive value is lower than about 0.05. Biomarkers having a low p-value can be used by themselves to classify individuals. Alternatively, combinations of two or more biomarkers can be used to classify individuals, where the combinations are chosen on the basis of the relative p-value of a biomarker. In general, those biomarkers with lower p-values are preferred for a given combination of biomarkers. Combinations of at least three, four, five, six, 10, 20 or 30 or more biomarkers also can be used to classify individuals in this manner. The artisan will understand that the relative p-value of any given biomarker may vary, depending on the size of the reference population.

Using the Wilcoxon Signed Rank Test, p-values were assigned to features from biomarker profiles obtained from biological samples taken at time 0, time—24 hours and time—48 hours. These p-values are listed in TABLES 8, 9 and 10, respectively.

TABLE 8 p-values from time 0 hours samples

| ion number | mhz (Da), retention time (min) | p-value |
|---|---|---|
| 1 | (179.0, 10.16) | 7.701965e−05 |
| 2 | (512.4, 10.44) | 1.112196e−04 |
| 3 | (371.3, 4.58) | 2.957102e−04 |
| 4 | (592.4, 15.69) | 3.790754e−04 |
| 5 | (363.2, 4.40) | 4.630887e−04 |
| 6 | (679.4, 5.92) | 1.261515e−03 |
| 7 | (835.0, 7.09) | 1.358581e−03 |
| 8 | (377.2, 4.61) | 1.641317e−03 |
| 9 | (490.3, 5.12) | 1.959479e−03 |
| 10 | (265.2, 4.72) | 3.138371e−03 |
| 11 | (627.3, 5.75) | 3.438053e−03 |
| 12 | (266.7, 14.83) | 3.470672e−03 |
| 13 | (774.9, 7.39) | 3.470672e−03 |
| 14 | (142.2, 3.38) | 4.410735e−03 |
| 15 | (142.0, −0.44) | 4.443662e−03 |
| 16 | (231.0, −0.41) | 5.080720e−03 |
| 17 | (451.3, 4.94) | 5.096689e−03 |
| 18 | (753.8, 9.34) | 5.097550e−03 |
| 19 | (399.2, 2.99) | 5.217724e−03 |
| 20 | (534.4, 10.53) | 5.877221e−03 |
| 21 | (978.8, 6.72) | 6.448607e−03 |
| 22 | (539.3, 5.30) | 6.651592e−03 |
| 23 | (492.2, 1.36) | 6.697313e−03 |
| 24 | (730.4, 6.54) | 6.724428e−03 |
| 25 | (842.6, 10.11) | 6.724428e−03 |
| 26 | (622.4, 5.61) | 7.249023e−03 |
| 27 | (331.7, 19.61) | 8.137318e−03 |
| 28 | (564.3, 14.16) | 8.419814e−03 |
| 29 | (415.3, 4.80) | 8.475773e−03 |
| 30 | (229.2, 2.39) | 8.604155e−03 |
| 31 | (118.2, 5.26) | 8.664167e−03 |
| 32 | (410.7, 0.77) | 8.664167e−03 |
| 33 | (733.5, 4.55) | 9.271924e−03 |
| 34 | (503.3, 5.12) | 9.413344e−03 |
| 35 | (453.2, 2.97) | 9.802539e−03 |
| 36 | (534.3, 5.30) | 1.089928e−02 |
| 37 | (459.3, 4.96) | 1.100198e−02 |
| 38 | (337.8, 5.51) | 1.136183e−02 |
| 39 | (525.4, 15.11) | 1.136183e−02 |
| 40 | (495.3, 18.52) | 1.282615e−02 |
| 41 | (763.4, 19.81) | 1.282615e−02 |
| 42 | (256.2, 6.03) | 1.286693e−02 |
| 43 | (319.1, 15.67) | 1.286693e−02 |
| 44 | (548.3, 5.24) | 1.286693e−02 |
| 45 | (858.8, 7.79) | 1.287945e−02 |
| 46 | (671.4, 5.77) | 1.310484e−02 |
| 47 | (353.2, 7.38) | 1.323194e−02 |
| 48 | (844.1, 9.68) | 1.333814e−02 |
| 49 | (421.2, 4.89) | 1.365072e−02 |
| 50 | (506.4, 19.65) | 1.438363e−02 |
| 51 | (393.3, 4.58) | 1.459411e−02 |
| 52 | (473.3, 5.12) | 1.518887e−02 |
| 53 | (189.1, 2.87) | 1.602381e−02 |
| 54 | (528.1, 16.18) | 1.603446e−02 |
| 55 | (137.2, 9.60) | 1.706970e−02 |
| 56 | (163.1, 10.98) | 1.706970e−02 |
| 57 | (176.1, 10.29) | 1.706970e−02 |
| 58 | (179.1, 6.23) | 1.706970e−02 |
| 59 | (271.5, 5.01) | 1.706970e−02 |
| 60 | (272.2, 6.49) | 1.706970e−02 |
| 61 | (399.3, 27.26) | 1.706970e−02 |
| 62 | (467.5, 5.95) | 1.706970e−02 |
| 63 | (478.0, 2.36) | 1.706970e−02 |
| 64 | (481.3, 26.85) | 1.706970e−02 |
| 65 | (931.9, 6.72) | 1.706970e−02 |
| 66 | (970.5, 7.00) | 1.706970e−02 |
| 67 | (763.2, 16.60) | 1.730862e−02 |
| 68 | (544.4, 15.56) | 1.732997e−02 |
| 69 | (666.4, 5.77) | 1.750379e−02 |
| 70 | (337.2, 9.32) | 1.812839e−02 |
| 71 | (407.2, 1.17) | 1.852695e−02 |
| 72 | (597.2, 5.32) | 1.895944e−02 |
| 73 | (333.1, 2.00) | 1.930165e−02 |
| 74 | (490.3, 13.78) | 1.989224e−02 |
| 75 | (139.1, 16.05) | 2.026959e−02 |
| 76 | (991.7, 16.60) | 2.046716e−02 |
| 77 | (814.2, 6.66) | 2.121091e−02 |
| 78 | (665.4, 15.46) | 2.127247e−02 |
| 79 | (875.9, 10.08) | 2.127247e−02 |
| 80 | (144.0, 0.25) | 2.137456e−02 |
| 81 | (622.7, 4.14) | 2.178625e−02 |
| 82 | (377.2, 12.32) | 2.240973e−02 |
| 83 | (509.3, 5.28) | 2.243384e−02 |
| 84 | (349.2, 2.69) | 2.252208e−02 |
| 85 | (302.0, 19.54) | 2.266635e−02 |
| 86 | (411.0, 2.20) | 2.303751e−02 |
| 87 | (296.2, 16.48) | 2.373348e−02 |
| 88 | (299.6, 15.62) | 2.440816e−02 |
| 89 | (162.1, 0.49) | 2.441678e−02 |
| 90 | (372.0, 0.62) | 2.472854e−02 |
| 91 | (377.2, 9.32) | 2.514306e−02 |
| 92 | (979.6, 10.14) | 2.530689e−02 |
| 93 | (417.3, 15.61) | 2.550843e−02 |
| 94 | (281.7, 19.54) | 2.563580e−02 |
| 95 | (276.2, 5.27) | 2.598704e−02 |
| 96 | (229.2, −0.79) | 2.626971e−02 |
| 97 | (346.1, 7.46) | 2.654063e−02 |
| 98 | (356.2, 9.88) | 2.654063e−02 |

TABLE 8-continued p-values from time 0 hours samples

| ion number | mhz (Da), retention time (min) | p-value |
|---|---|---|
| 99 | (616.4, 8.05) | 2.683578e−02 |
| 100 | (850.4, 7.65) | 2.697931e−02 |
| 101 | (495.3, 5.12) | 2.712924e−02 |
| 102 | (446.3, 4.94) | 2.739049e−02 |
| 103 | (476.3, 1.86) | 2.770535e−02 |
| 104 | (520.4, 5.12) | 2.774232e−02 |
| 105 | (428.3, 6.20) | 2.808469e−02 |
| 106 | (536.3, 17.97) | 2.863714e−02 |
| 107 | (860.3, 6.94) | 2.894386e−02 |
| 108 | (762.9, 16.65) | 2.958886e−02 |
| 109 | (788.9, 6.43) | 2.967800e−02 |
| 110 | (970.1, 6.47) | 2.967800e−02 |
| 111 | (853.8, 5.77) | 3.039550e−02 |
| 112 | (913.6, 9.50) | 3.039550e−02 |
| 113 | (407.2, 4.72) | 3.041346e−02 |
| 114 | (335.2, 16.10) | 3.047982e−02 |
| 115 | (331.2, 12.93) | 3.075216e−02 |
| 116 | (512.3, 13.80) | 3.075216e−02 |
| 117 | (895.8, 6.80) | 3.084773e−02 |
| 118 | (120.2, 8.37) | 3.110972e−02 |
| 119 | (238.2, 9.32) | 3.110972e−02 |
| 120 | (506.3, 8.10) | 3.110972e−02 |
| 121 | (949.9, 6.66) | 3.115272e−02 |
| 122 | (176.1, 6.96) | 3.161957e−02 |
| 123 | (664.9, 2.41) | 3.275550e−02 |
| 124 | (551.4, 18.56) | 3.290912e−02 |
| 125 | (459.0, 5.98) | 3.389516e−02 |
| 126 | (811.5, 7.73) | 3.389516e−02 |
| 127 | (919.9, 10.01) | 3.414450e−02 |
| 128 | (547.4, 5.28) | 3.444290e−02 |
| 129 | (895.4, 6.62) | 3.460947e−02 |
| 130 | (132.2, 0.79) | 3.549773e−02 |
| 131 | (944.8, 9.65) | 3.567313e−02 |
| 132 | (730.7, 6.46) | 3.581882e−02 |
| 133 | (529.5, 16.70) | 3.666990e−02 |
| 134 | (449.3, 24.40) | 3.687266e−02 |
| 135 | (465.3, 5.08) | 3.725633e−02 |
| 136 | (481.3, 4.96) | 3.956117e−02 |
| 137 | (250.1, 14.23) | 3.982131e−02 |
| 138 | (565.3, 16.05) | 3.982131e−02 |
| 139 | (559.0, 15.30) | 3.994530e−02 |
| 140 | (555.3, 4.18) | 4.078620e−02 |
| 141 | (568.4, 15.49) | 4.118355e−02 |
| 142 | (120.0, 11.52) | 4.145499e−02 |
| 143 | (120.2, 14.91) | 4.145499e−02 |
| 144 | (167.0, 5.00) | 4.145499e−02 |
| 145 | (173.0, 19.96) | 4.145499e−02 |
| 146 | (324.9, 2.27) | 4.145499e−02 |
| 147 | (328.8, 19.98) | 4.145499e−02 |
| 148 | (345.7, 16.95) | 4.145499e−02 |
| 149 | (407.2, 12.07) | 4.145499e−02 |
| 150 | (478.3, 3.69) | 4.145499e−02 |
| 151 | (484.2, 8.40) | 4.145499e−02 |
| 152 | (502.2, 4.55) | 4.145499e−02 |
| 153 | (597.4, 11.40) | 4.145499e−02 |
| 154 | (612.3, 6.40) | 4.145499e−02 |
| 155 | (700.3, 9.40) | 4.145499e−02 |
| 156 | (730.5, 11.63) | 4.145499e−02 |
| 157 | (771.4, 6.02) | 4.145499e−02 |
| 158 | (811.9, 10.99) | 4.145499e−02 |
| 159 | (859.9, 2.47) | 4.145499e−02 |
| 160 | (450.3, 11.99) | 4.145499e−02 |
| 161 | (619.3, 11.42) | 4.165835e−02 |
| 162 | (102.1, 6.16) | 4.238028e−02 |
| 163 | (717.5, 9.11) | 4.238028e−02 |
| 164 | (606.0, 7.63) | 4.317929e−02 |
| 165 | (627.2, 2.48) | 4.317929e−02 |
| 166 | (252.1, 6.62) | 4.318649e−02 |
| 167 | (657.5, 5.53) | 4.332436e−02 |
| 168 | (635.7, 7.94) | 4.399442e−02 |
| 169 | (167.2, 14.42) | 4.452609e−02 |
| 170 | (812.5, 10.24) | 4.528236e−02 |
| 171 | (575.4, 10.00) | 4.533566e−02 |
| 172 | (379.3, 15.55) | 4.644328e−02 |
| 173 | (468.3, 13.44) | 4.644328e−02 |
| 174 | (295.3, 16.10) | 4.721618e−02 |
| 175 | (715.8, 7.68) | 4.736932e−02 |
| 176 | (810.6, 19.21) | 4.759452e−02 |
| 177 | (159.1, 13.02) | 4.795773e−02 |
| 178 | (435.2, 0.83) | 4.795773e−02 |
| 179 | (443.0, 11.99) | 4.795773e−02 |
| 180 | (468.4, 19.65) | 4.795773e−02 |
| 181 | (909.8, 9.52) | 4.795773e−02 |
| 182 | (647.2, 2.45) | 4.838671e−02 |
| 183 | (564.4, 5.28) | 4.958429e−02 |

TABLE 9 p-values from time-24 hours samples

| ion number | m/z (Da), retention time (min) | p-value |
|---|---|---|
| 1 | (265.2, 4.72) | 0.0003368072 |
| 2 | (785.5, 9.30) | 0.0006770673 |
| 3 | (685.1, 6.85) | 0.0010222902 |
| 4 | (608.4, 5.39) | 0.0014633974 |
| 5 | (141.1, 5.13) | 0.0018265874 |
| 6 | (652.5, 5.51) | 0.0022097623 |
| 7 | (228.0, 3.12) | 0.0029411592 |
| 8 | (660.1, 3.90) | 0.0032802432 |
| 9 | (235.1, 4.04) | 0.0038917632 |
| 10 | (287.1, 4.72) | 0.0045802571 |
| 11 | (141.2, 1.46) | 0.0049063026 |
| 12 | (553.3, 5.38) | 0.0053961549 |
| 13 | (114.2, 2.49) | 0.0060009121 |
| 14 | (490.3, 5.12) | 0.0064288387 |
| 15 | (142.0, −0.44) | 0.0064784467 |
| 16 | (428.3, 6.20) | 0.0064784467 |
| 17 | (564.4, 5.28) | 0.0081876219 |
| 18 | (678.8, 2.37) | 0.0089256763 |
| 19 | (155.1, 2.87) | 0.0091072246 |
| 20 | (377.2, 4.61) | 0.0098626515 |
| 21 | (221.0, 1.92) | 0.0102589726 |
| 22 | (463.2, 1.88) | 0.0102589726 |
| 23 | (142.2, 3.38) | 0.0106568532 |
| 24 | (231.0, −0.41) | 0.0106568532 |
| 25 | (256.2, 6.03) | 0.0106568532 |
| 26 | (597.2, 2.05) | 0.0106568532 |
| 27 | (638.8, 2.35) | 0.0112041041 |
| 28 | (800.6, 1.53) | 0.0112041041 |
| 29 | (385.3, 24.07) | 0.0113535538 |
| 30 | (578.4, 5.46) | 0.0114707005 |
| 31 | (352.3, 11.76) | 0.0115864528 |
| 32 | (858.2, 10.41) | 0.0115864528 |
| 33 | (889.7, 16.16) | 0.0115864528 |
| 34 | (190.1, 3.99) | 0.0120870451 |
| 35 | (493.3, 26.36) | 0.0120870451 |
| 36 | (608.3, 2.35) | 0.0122930750 |
| 37 | (958.8, 6.36) | 0.0127655270 |
| 38 | (235.0, 0.51) | 0.0128665507 |
| 39 | (739.5, 9.45) | 0.0139994021 |
| 40 | (525.2, 1.92) | 0.0141261152 |
| 41 | (372.4, 11.66) | 0.0148592431 |
| 42 | (415.3, 4.80) | 0.0154439839 |
| 43 | (439.2, 9.40) | 0.0154583510 |
| 44 | (819.0, 2.11) | 0.0156979793 |
| 45 | (459.3, 20.83) | 0.0161386158 |
| 46 | (372.2, 5.10) | 0.0169489151 |
| 47 | (875.4, 19.37) | 0.0170124705 |
| 48 | (989.2, 10.14) | 0.0184799654 |
| 49 | (179.0, 10.16) | 0.0190685234 |
| 50 | (231.0, 6.41) | 0.0191486950 |
| 51 | (460.9, 1.77) | 0.0194721634 |
| 52 | (813.5, 9.83) | 0.0194721634 |

TABLE 9-continued p-values from time-24 hours samples

| ion number | m/z (Da), retention time (min) | p-value |
|---|---|---|
| 53 | (274.2, 4.67) | 0.0194863889 |
| 54 | (158.2, 10.93) | 0.0203661514 |
| 55 | (676.7, 1.07) | 0.0208642732 |
| 56 | (171.2, 25.87) | 0.0213201435 |
| 57 | (520.4, 5.12) | 0.0214439678 |
| 58 | (523.3, 22.32) | 0.0216203784 |
| 59 | (329.0, 1.27) | 0.0222231947 |
| 60 | (585.2, 15.27) | 0.0222231947 |
| 61 | (534.3, 5.30) | 0.0224713144 |
| 62 | (349.2, 2.69) | 0.0234305681 |
| 63 | (263.2, 5.05) | 0.0240107773 |
| 64 | (278.1, 5.24) | 0.0240107773 |
| 65 | (425.9, 6.20) | 0.0240107773 |
| 66 | (575.4, 10.00) | 0.0240107773 |
| 67 | (649.3, 5.75) | 0.0240107773 |
| 68 | (152.1, 1.51) | 0.0244163058 |
| 69 | (785.1, 9.29) | 0.0244163058 |
| 70 | (509.3, 5.28) | 0.0257388421 |
| 71 | (525.4, 15.11) | 0.0259747750 |
| 72 | (261.2, 21.02) | 0.0259960666 |
| 73 | (914.1, 10.04) | 0.0260109531 |
| 74 | (465.3, 5.08) | 0.0260926970 |
| 75 | (433.3, 18.18) | 0.0271021410 |
| 76 | (300.0, 21.90) | 0.0275140464 |
| 77 | (811.6, 19.44) | 0.0276109304 |
| 78 | (710.5, 5.90) | 0.0295828987 |
| 79 | (569.2, 2.00) | 0.0302737381 |
| 80 | (388.3, 4.58) | 0.0308414401 |
| 81 | (173.1, 6.52) | 0.0308972074 |
| 82 | (266.7, 14.83) | 0.0308972074 |
| 83 | (286.2, 12.60) | 0.0308972074 |
| 84 | (619.3, 19.04) | 0.0308972074 |
| 85 | (682.6, 9.44) | 0.0308972074 |
| 86 | (717.3, 17.96) | 0.0308972074 |
| 87 | (920.6, 10.61) | 0.0308972074 |
| 88 | (988.4, 10.46) | 0.0308972074 |
| 89 | (271.1, 15.08) | 0.0313675727 |
| 90 | (740.5, 6.02) | 0.0316777607 |
| 91 | (839.6, 20.85) | 0.0316777607 |
| 92 | (610.9, 2.44) | 0.0329765016 |
| 93 | (179.1, 13.20) | 0.0330555292 |
| 94 | (701.4, 5.63) | 0.0330555292 |
| 95 | (175.1, 8.49) | 0.0332024906 |
| 96 | (279.0, 2.32) | 0.0337986949 |
| 97 | (670.4, 9.09) | 0.0337986949 |
| 98 | (415.3, 15.42) | 0.0338750641 |
| 99 | (183.1, 6.88) | 0.0343045905 |
| 100 | (160.1, 0.50) | 0.0344826274 |
| 101 | (459.3, 4.96) | 0.0352364197 |
| 102 | (305.2, 1.87) | 0.0353424937 |
| 103 | (216.2, 4.54) | 0.0363303150 |
| 104 | (603.3, 6.48) | 0.0363303150 |
| 105 | (914.1, 6.94) | 0.0368261384 |
| 106 | (205.1, 6.75) | 0.0368844784 |
| 107 | (446.3, 4.94) | 0.0371476565 |
| 108 | (513.1, 4.48) | 0.0380144912 |
| 109 | (676.0, 6.65) | 0.0382429645 |
| 110 | (366.1, 0.86) | 0.0383351335 |
| 111 | (227.9, −0.44) | 0.0386073936 |
| 112 | (641.4, 7.27) | 0.0387953825 |
| 113 | (395.2, 24.02) | 0.0388820140 |
| 114 | (929.6, 7.27) | 0.0389610390 |
| 115 | (371.3, 4.58) | 0.0392271166 |
| 116 | (402.2, 1.19) | 0.0392271166 |
| 117 | (127.0, 4.75) | 0.0397364228 |
| 118 | (193.0, 1.36) | 0.0404560651 |
| 119 | (194.0, 1.00) | 0.0404560651 |
| 120 | (379.3, 15.55) | 0.0404560651 |
| 121 | (495.3, 12.82) | 0.0404560651 |
| 122 | (823.4, 9.50) | 0.0404560651 |
| 123 | (235.1, 8.53) | 0.0405335640 |
| 124 | (476.4, 4.96) | 0.0421855472 |
| 125 | (472.5, 11.18) | 0.0425955352 |
| 126 | (693.1, 5.95) | 0.0426922311 |
| 127 | (274.1, 7.80) | 0.0428211411 |
| 128 | (402.2, 12.86) | 0.0428660082 |
| 129 | (746.8, 2.42) | 0.0429101967 |
| 130 | (801.0, 2.11) | 0.0429101967 |
| 131 | (366.7, 5.89) | 0.0434178862 |
| 132 | (458.4, 4.70) | 0.0434178862 |
| 133 | (369.4, 26.36) | 0.0440035652 |
| 134 | (601.0, 0.43) | 0.0440035652 |
| 135 | (249.2, 6.55) | 0.0440434139 |
| 136 | (666.4, 5.77) | 0.0444571249 |
| 137 | (415.4, 12.38) | 0.0447164378 |
| 138 | (652.1, 5.87) | 0.0447164378 |
| 139 | (472.2, 11.12) | 0.0453906033 |
| 140 | (441.4, 24.91) | 0.0464361698 |
| 141 | (575.4, 20.88) | 0.0464361698 |
| 142 | (393.3, 4.58) | 0.0464768588 |
| 143 | (620.7, 0.74) | 0.0465716607 |
| 144 | (842.9, 6.93) | 0.0465716607 |
| 145 | (685.4, 17.53) | 0.0468826130 |
| 146 | (476.3, 1.86) | 0.0472378721 |
| 147 | (399.2, 2.99) | 0.0479645296 |
| 148 | (211.1, 13.48) | 0.0488051357 |
| 149 | (357.3, 9.11) | 0.0488051357 |
| 150 | (313.2, 17.63) | 0.0495881957 |

TABLE 10 p-values from time-48 hours samples

| ion number | m/z (Da), retention time (min) | p-value |
|---|---|---|
| 1 | (845.2, 6.33) | 0.001343793 |
| 2 | (715.8, 7.68) | 0.002669885 |
| 3 | (745.7, 6.03) | 0.002743002 |
| 4 | (802.4, 8.16) | 0.002822379 |
| 5 | (648.5, −0.24) | 0.003721455 |
| 6 | (745.3, 6.02) | 0.005142191 |
| 7 | (608.4, 5.39) | 0.005491954 |
| 8 | (265.2, 4.72) | 0.006272684 |
| 9 | (505.3, 12.78) | 0.006518681 |
| 10 | (371.3, 4.58) | 0.006931949 |
| 11 | (261.2, 1.26) | 0.008001346 |
| 12 | (971.4, 10.51) | 0.008726088 |
| 13 | (152.1, 1.51) | 0.009174244 |
| 14 | (685.1, 6.85) | 0.009704974 |
| 15 | (456.4, 9.80) | 0.010451432 |
| 16 | (214.2, 15.68) | 0.010792220 |
| 17 | (446.0, 2.54) | 0.010792220 |
| 18 | (346.1, 7.46) | 0.011152489 |
| 19 | (227.0, 23.11) | 0.011834116 |
| 20 | (407.2, 1.17) | 0.011946593 |
| 21 | (435.3, 19.92) | 0.011946593 |
| 22 | (451.3, 4.94) | 0.012261329 |
| 23 | (274.1, 7.80) | 0.012266073 |
| 24 | (869.0, 9.70) | 0.012303709 |
| 25 | (274.2, 4.67) | 0.012859736 |
| 26 | (789.4, 6.11) | 0.012890139 |
| 27 | (576.4, 3.29) | 0.013087923 |
| 28 | (930.0, 9.75) | 0.013087923 |
| 29 | (512.4, 10.44) | 0.014315178 |
| 30 | (878.9, 7.28) | 0.014513409 |
| 31 | (503.3, 5.12) | 0.015193810 |
| 32 | (180.1, 4.54) | 0.015226001 |
| 33 | (209.1, 5.03) | 0.015254389 |
| 34 | (616.2, 11.90) | 0.016782325 |
| 35 | (443.3, 3.41) | 0.017490379 |
| 36 | (572.6, 4.30) | 0.017654283 |
| 37 | (931.9, 6.72) | 0.018138469 |
| 38 | (966.4, 10.49) | 0.019031437 |
| 39 | (541.3, 5.12) | 0.019316716 |

TABLE 10-continued p-values from time-48 hours samples

| ion number | m/z (Da), retention time (min) | p-value |
|---|---|---|
| 40 | (470.3, 10.72) | 0.019821985 |
| 41 | (281.3, 16.88) | 0.020436455 |
| 42 | (407.2, 4.72) | 0.021104001 |
| 43 | (627.2, 2.48) | 0.021491454 |
| 44 | (313.2, 6.31) | 0.022912878 |
| 45 | (173.2, 15.68) | 0.023189016 |
| 46 | (675.6, 5.75) | 0.023820433 |
| 47 | (137.2, 9.60) | 0.023895386 |
| 48 | (357.2, 5.65) | 0.023895386 |
| 49 | (372.0, 0.62) | 0.023895386 |
| 50 | (635.3, 2.38) | 0.023895386 |
| 51 | (743.8, 4.55) | 0.023895386 |
| 52 | (185.2, 6.29) | 0.024742907 |
| 53 | (930.4, 7.60) | 0.024770578 |
| 54 | (564.4, 5.28) | 0.024811749 |
| 55 | (415.2, 9.09) | 0.025574438 |
| 56 | (697.3, 16.10) | 0.025714289 |
| 57 | (657.3, 2.49) | 0.025825394 |
| 58 | (996.1, 9.94) | 0.026026402 |
| 59 | (185.0, 0.10) | 0.027530406 |
| 60 | (333.1, 2.00) | 0.027840095 |
| 61 | (611.3, 6.59) | 0.028096875 |
| 62 | (283.3, 18.53) | 0.028392609 |
| 63 | (506.3, 8.10) | 0.028392609 |
| 64 | (726.4, 5.67) | 0.028392609 |
| 65 | (397.3, 20.91) | 0.029361285 |
| 66 | (311.9, 2.10) | 0.029433328 |
| 67 | (473.3, 8.15) | 0.029433328 |
| 68 | (490.2, 8.85) | 0.029433328 |
| 69 | (493.3, 22.99) | 0.029433328 |
| 70 | (577.2, 3.56) | 0.029433328 |
| 71 | (653.7, 6.16) | 0.029433328 |
| 72 | (757.5, 16.28) | 0.029433328 |
| 73 | (819.0, 2.11) | 0.029433328 |
| 74 | (853.5, 13.13) | 0.029433328 |
| 75 | (889.2, 6.42) | 0.029433328 |
| 76 | (929.6, 10.60) | 0.029433328 |
| 77 | (963.3, 9.70) | 0.029433328 |
| 78 | (982.1, 9.39) | 0.029433328 |
| 79 | (446.3, 4.94) | 0.030176399 |
| 80 | (959.5, 10.86) | 0.030176399 |
| 81 | (169.1, 5.03) | 0.030177290 |
| 82 | (906.7, 9.75) | 0.030212739 |
| 83 | (772.1, 7.79) | 0.030482971 |
| 84 | (857.0, 9.70) | 0.030966151 |
| 85 | (861.8, 9.74) | 0.030966151 |
| 86 | (377.2, 12.32) | 0.031285164 |
| 87 | (229.2, −0.79) | 0.031539774 |
| 88 | (229.2, 2.39) | 0.031539774 |
| 89 | (740.4, 9.58) | 0.031759640 |
| 90 | (958.3, 9.66) | 0.031759640 |
| 91 | (739.5, 18.01) | 0.032714845 |
| 92 | (377.2, 4.61) | 0.032818612 |
| 93 | (144.0, 0.25) | 0.032941894 |
| 94 | (459.3, 4.96) | 0.033735985 |
| 95 | (715.8, 4.37) | 0.034116302 |
| 96 | (649.0, 2.13) | 0.034332004 |
| 97 | (776.3, 6.78) | 0.034520017 |
| 98 | (827.1, 9.58) | 0.034662245 |
| 99 | (439.2, 9.40) | 0.035385909 |
| 100 | (376.0, 2.11) | 0.038036916 |
| 101 | (734.6, 7.21) | 0.038036916 |
| 102 | (402.2, 1.19) | 0.038177664 |
| 103 | (740.5, 6.02) | 0.038356830 |
| 104 | (502.5, 4.01) | 0.038481929 |
| 105 | (694.4, 6.02) | 0.039047025 |
| 106 | (331.0, 0.74) | 0.039943461 |
| 107 | (302.1, 4.44) | 0.040965049 |
| 108 | (836.1, 8.31) | 0.041276236 |
| 109 | (909.4, 9.75) | 0.041642229 |
| 110 | (358.0, 2.13) | 0.041676687 |
| 111 | (502.2, 4.55) | 0.042049098 |
| 112 | (302.2, 0.79) | 0.042062826 |
| 113 | (936.9, 9.51) | 0.042143408 |
| 114 | (492.2, 1.36) | 0.042286848 |
| 115 | (204.2, 5.03) | 0.043172669 |
| 116 | (701.4, 5.63) | 0.044132315 |
| 117 | (373.3, 24.05) | 0.045041891 |
| 118 | (657.4, 5.53) | 0.045102516 |
| 119 | (357.3, 15.86) | 0.045170280 |
| 120 | (670.9, 6.71) | 0.045249625 |
| 121 | (850.0, 7.56) | 0.046346695 |
| 122 | (576.4, 16.02) | 0.046573286 |
| 123 | (670.4, 9.09) | 0.046609659 |
| 124 | (578.4, 5.46) | 0.047297957 |
| 125 | (525.3, 5.12) | 0.047503607 |
| 126 | (926.0, 6.12) | 0.047503607 |
| 127 | (987.3, 9.56) | 0.047882538 |
| 128 | (231.0, −0.41) | 0.048437237 |
| 129 | (608.3, 2.35) | 0.048607203 |
| 130 | (966.7, 10.60) | 0.048825822 |

A nonparametric test (e.g., a Wilcoxon Signed Rank Test) alternatively can be used to find p-values for features that are based on the progressive appearance or disappearance of the feature in populations that are progressing toward sepsis. In this form of the test, a baseline value for a given feature first is measured, using the data from the time of entry into the study (Day 1 samples) for the sepsis and SIRS groups. The feature intensity in sepsis and SIRS samples is then compared in, for example, time—48 hour samples to determine whether the feature intensity has increased or decreased from its baseline value. Finally, p-values are assigned to the difference from baseline in a feature intensity in the sepsis populations versus the SIRS populations. The following p-values, listed in TABLES 11-13, were obtained when measuring these differences from baseline in p-values.

TABLE 11 p-values for features differenced from baseline: time 0 hours samples

| ion number | m/z (Da), retention time (min) | p-value |
|---|---|---|
| 1 | (991.7, 16.6) | 0.000225214 |
| 2 | (592.4, 15.69) | 0.001008201 |
| 3 | (733.5, 4.55) | 0.001363728 |
| 4 | (173.1, 23.44) | 0.001696095 |
| 5 | (763.2, 16.6) | 0.001851633 |
| 6 | (932.2, 6.72) | 0.002380877 |
| 7 | (842.6, 10.11) | 0.002575890 |
| 8 | (295.9, 15.78) | 0.002799236 |
| 9 | (512.4, 10.44) | 0.004198319 |
| 10 | (551.4, 24.89) | 0.005132229 |
| 11 | (167.1, 10.99) | 0.005168091 |
| 12 | (857.8, 8.21) | 0.005209485 |
| 13 | (763.4, 19.81) | 0.005541078 |
| 14 | (931.9, 6.72) | 0.006142506 |
| 15 | (167.2, 14.42) | 0.006349154 |
| 16 | (510.4, 17.91) | 0.006427070 |
| 17 | (295.3, 16.1) | 0.007165849 |
| 18 | (353.2, 7.38) | 0.007255100 |
| 19 | (653, 6.71) | 0.007848203 |
| 20 | (730.4, 6.54) | 0.008402925 |
| 21 | (142, 0.44) | 0.008578959 |
| 22 | (331.7, 19.61) | 0.008807931 |
| 23 | (386.3, 9.47) | 0.009227968 |
| 24 | (524.4, 19.33) | 0.010256841 |
| 25 | (741.5, 23.22) | 0.010329009 |
| 26 | (272.2, 6.49) | 0.010345274 |
| 27 | (448.3, 9.24) | 0.010666648 |
| 28 | (713.5, 21.99) | 0.011150954 |

TABLE 11-continued p-values for features differenced from baseline: time 0 hours samples

| ion number | m/z (Da), retention time (min) | p-value |
|---|---|---|
| 29 | (353.3, 22.38) | 0.011224096 |
| 30 | (457.2, 0.88) | 0.011653586 |
| 31 | (708.9, 0.37) | 0.012197946 |
| 32 | (256.2, 6.03) | 0.013251532 |
| 33 | (721.4, 23.49) | 0.014040014 |
| 34 | (496.4, 16.6) | 0.014612622 |
| 35 | (634.9, 27.04) | 0.015093015 |
| 36 | (663.3, 2.06) | 0.015093015 |
| 37 | (679.4, 5.92) | 0.015176669 |
| 38 | (521.4, 23.84) | 0.015526731 |
| 39 | (358.3, 4.4) | 0.015795031 |
| 40 | (409.2, 6.95) | 0.015875221 |
| 41 | (537.3, 23) | 0.016202704 |
| 42 | (875.4, 19.37) | 0.016372468 |
| 43 | (875.9, 10.08) | 0.016391836 |
| 44 | (265.2, 9.37) | 0.016924737 |
| 45 | (450.3, 11.99) | 0.017293769 |
| 46 | (329, 1.27) | 0.017732659 |
| 47 | (534.4, 10.53) | 0.018580510 |
| 48 | (616.2, 11.9) | 0.018703298 |
| 49 | (177, 0.93) | 0.018855039 |
| 50 | (772.1, 16.51) | 0.018991142 |
| 51 | (424.2, 6.12) | 0.019195215 |
| 52 | (277.3, 21.72) | 0.020633230 |
| 53 | (333.2, 7.39) | 0.020898404 |
| 54 | (742.8, 4.02) | 0.021093249 |
| 55 | (428.3, 6.2) | 0.021697014 |
| 56 | (946, 10.49) | 0.021935440 |
| 57 | (970.5, 7) | 0.021999796 |
| 58 | (281.7, 19.54) | 0.022055564 |
| 59 | (568.4, 15.49) | 0.022208535 |
| 60 | (700.3, 9.4) | 0.022500138 |
| 61 | (118.2, 5.26) | 0.022773904 |
| 62 | (601.3, 5.46) | 0.023578505 |
| 63 | (818.3, 7.18) | 0.023788872 |
| 64 | (799.4, 9.64) | 0.023906673 |
| 65 | (244.1, 2.22) | 0.024125162 |
| 66 | (145.1, 3.99) | 0.024385288 |
| 67 | (328.8, 19.98) | 0.024385288 |
| 68 | (342.4, 13.41) | 0.025034251 |
| 69 | (356.2, 5.6) | 0.025034251 |
| 70 | (321.3, 19.96) | 0.025128604 |
| 71 | (523.3, 13.8) | 0.025164665 |
| 72 | (504.3, 15.49) | 0.025894254 |
| 73 | (842.3, 10.76) | 0.026070176 |
| 74 | (585.3, 25.35) | 0.026196933 |
| 75 | (176.1, 10.29) | 0.027193290 |
| 76 | (399.3, 27.26) | 0.027193290 |
| 77 | (761.8, 7.89) | 0.027193290 |
| 78 | (909.8, 9.52) | 0.027193290 |
| 79 | (291.2, 12.57) | 0.029135281 |
| 80 | (715.8, 7.68) | 0.030440991 |
| 81 | (546.4, 19.33) | 0.030479818 |
| 82 | (795.5, 20.72) | 0.030479818 |
| 83 | (321, 19.53) | 0.030693238 |
| 84 | (746.8, 10.2) | 0.030888031 |
| 85 | (831.5, 20.87) | 0.030888031 |
| 86 | (872.9, 11.6) | 0.030888031 |
| 87 | (598, 8.58) | 0.031026286 |
| 88 | (407.2, 12.07) | 0.031941032 |
| 89 | (645.3, 13.42) | 0.031941032 |
| 90 | (662.1, 8.16) | 0.031941032 |
| 91 | (179, 10.16) | 0.032126841 |
| 92 | (779.5, 19.79) | 0.032301988 |
| 93 | (171.2, 25.87) | 0.032868402 |
| 94 | (979.6, 10.14) | 0.033098647 |
| 95 | (245.2, 22.24) | 0.033117202 |
| 96 | (370.3, 2.3) | 0.033696034 |
| 97 | (433.3, 5.29) | 0.033696034 |
| 98 | (771.4, 10.01) | 0.033696034 |
| 99 | (876.3, 9.94) | 0.033696034 |
| 100 | (893, 7.09) | 0.033919037 |
| 101 | (669.2, 2.13) | 0.034234876 |
| 102 | (643.3, 5.67) | 0.034557232 |
| 103 | (991.3, 9.72) | 0.035680492 |
| 104 | (577.5, 16.48) | 0.036136938 |
| 105 | (820, 6.38) | 0.036179853 |
| 106 | (856.6, 10.29) | 0.036179853 |
| 107 | (453.2, 6.62) | 0.036689053 |
| 108 | (652.1, 5.87) | 0.037082670 |
| 109 | (944.8, 9.65) | 0.037337126 |
| 110 | (494.4, 14.75) | 0.037526457 |
| 111 | (185, 11.17) | 0.037568360 |
| 112 | (229.2, 0.79) | 0.037574432 |
| 113 | (245.1, 11.44) | 0.038031041 |
| 114 | (279.3, 20.72) | 0.038253242 |
| 115 | (781.5, 20.04) | 0.038253242 |
| 116 | (409.4, 22.56) | 0.038673618 |
| 117 | (315.2, 14.29) | 0.039895232 |
| 118 | (759.5, 9.33) | 0.040499878 |
| 119 | (995.1, 9.94) | 0.040516802 |
| 120 | (848.3, 9.66) | 0.040554157 |
| 121 | (263.3, 22.26) | 0.041183545 |
| 122 | (267.7, 16.55) | 0.041183545 |
| 123 | (544.4, 15.56) | 0.041183545 |
| 124 | (617.5, 17.71) | 0.041406719 |
| 125 | (411.5, 1.06) | 0.041454989 |
| 126 | (597.4, 11.4) | 0.041454989 |
| 127 | (771.4, 6.02) | 0.041454989 |
| 128 | (901.9, 1.03) | 0.041454989 |
| 129 | (415.2, 9.09) | 0.041542794 |
| 130 | (430.3, 9.1) | 0.041922297 |
| 131 | (414.3, 4.29) | 0.043298568 |
| 132 | (414.9, 5.86) | 0.043427801 |
| 133 | (444.2, 6) | 0.043665836 |
| 134 | (505.3, 12.78) | 0.043665836 |
| 135 | (231, 0.41) | 0.043722631 |
| 136 | (370.3, 10.79) | 0.044296546 |
| 137 | (653.5, 19.99) | 0.044296546 |
| 138 | (291.7, 15.37) | 0.044815129 |
| 139 | (531.3, 21.48) | 0.044870846 |
| 140 | (715.4, 5.89) | 0.044985107 |
| 141 | (327.3, 16.98) | 0.045218533 |
| 142 | (499.4, 15.11) | 0.046077647 |
| 143 | (766.2, 15.77) | 0.046332971 |
| 144 | (664.2, 11.84) | 0.047191074 |
| 145 | (567.4, 20.79) | 0.047549465 |
| 146 | (809.6, 21.33) | 0.047600425 |
| 147 | (393.3, 21.08) | 0.048014243 |
| 148 | (754.6, 7.21) | 0.048520560 |
| 149 | (298.3, 24.36) | 0.049732041 |
| 150 | (883.3, 6.69) | 0.049768492 |
| 151 | (468.3, 13.44) | 0.049813626 |
| 152 | (665.4, 15.46) | 0.049918030 |

TABLE 12 p-values for features differenced from baseline: time-24 hours samples

| ion number | m/z (Da), retention time (min) | p-value |
|---|---|---|
| 1 | (875.4, 19.37) | 0.0006856941 |
| 2 | (256.2, 6.03) | 0.0009911606 |
| 3 | (228, 3.12) | 0.0014153532 |
| 4 | (227.9, 0.44) | 0.0015547019 |
| 5 | (879.8, 4.42) | 0.0025072593 |
| 6 | (858.2, 10.41) | 0.0029384997 |
| 7 | (159, 2.37) | 0.0038991631 |
| 8 | (186.9, 2.44) | 0.0045074080 |
| 9 | (609.1, 1.44) | 0.0047227895 |
| 10 | (996.1, 9.94) | 0.0058177265 |
| 11 | (430.7, 4.21) | 0.0063024974 |
| 12 | (141.1, 5.13) | 0.0068343584 |

TABLE 12-continued p-values for features differenced from baseline: time-24 hours samples

| ion number | m/z (Da), retention time (min) | p-value |
| --- | --- | --- |
| 13 | (839.6, 20.85) | 0.0072422001 |
| 14 | (956.1, 10.62) | 0.0080620376 |
| 15 | (113.2, 0.44) | 0.0081626136 |
| 16 | (428.3, 6.2) | 0.0081962770 |
| 17 | (802.9, 0.39) | 0.0081962770 |
| 18 | (819, 2.11) | 0.0081968739 |
| 19 | (366.1, 0.86) | 0.0084072673 |
| 20 | (993.5, 9.39) | 0.0084773116 |
| 21 | (919.5, 9.63) | 0.0098988701 |
| 22 | (680.6, 7.39) | 0.0105489986 |
| 23 | (523.3, 22.32) | 0.0105995251 |
| 24 | (668.3, 8.45) | 0.0112292667 |
| 25 | (463.2, 1.88) | 0.0113722034 |
| 26 | (259, 11.71) | 0.0115252694 |
| 27 | (889.7, 16.16) | 0.0115864528 |
| 28 | (810.4, 7.42) | 0.0119405153 |
| 29 | (300, 21.9) | 0.0123871653 |
| 30 | (141.2, 1.46) | 0.0124718161 |
| 31 | (785.5, 9.3) | 0.0126735996 |
| 32 | (660.1, 3.9) | 0.0131662199 |
| 33 | (575.4, 10) | 0.0133539242 |
| 34 | (398.2, 8.89) | 0.0133977345 |
| 35 | (678.8, 2.37) | 0.0134811753 |
| 36 | (779.5, 19.79) | 0.0152076628 |
| 37 | (190.1, 3.99) | 0.0153485356 |
| 38 | (746.8, 2.42) | 0.0153591871 |
| 39 | (407.2, 7.81) | 0.0154972293 |
| 40 | (265.2, 9.37) | 0.0163877868 |
| 41 | (447.8, 6.29) | 0.0163877868 |
| 42 | (472.5, 11.18) | 0.0166589145 |
| 43 | (951.9, 10.21) | 0.0169717792 |
| 44 | (138.2, 10.13) | 0.0170020893 |
| 45 | (739.5, 9.45) | 0.0171771560 |
| 46 | (999, 7.71) | 0.0177981470 |
| 47 | (472.2, 11.12) | 0.0178902225 |
| 48 | (138.1, 1.89) | 0.0180631050 |
| 49 | (842.9, 6.93) | 0.0189332371 |
| 50 | (717.3, 17.96) | 0.0193107546 |
| 51 | (245.2, 5.23) | 0.0201247940 |
| 52 | (666.4, 9.29) | 0.0211733529 |
| 53 | (820, 6.38) | 0.0216512533 |
| 54 | (991.7, 9.21) | 0.0219613529 |
| 55 | (177, 0.93) | 0.0223857280 |
| 56 | (488.3, 9.68) | 0.0224061094 |
| 57 | (119.1, 9.19) | 0.0224206599 |
| 58 | (278.1, 5.24) | 0.0240107773 |
| 59 | (409.2, 6.95) | 0.0256235918 |
| 60 | (369.2, 3.37) | 0.0259379108 |
| 61 | (482.4, 19.26) | 0.0261591305 |
| 62 | (806.6, 21.29) | 0.0269790713 |
| 63 | (637.9, 7.43) | 0.0273533420 |
| 64 | (373.3, 11.45) | 0.0277220597 |
| 65 | (264.2, 8.83) | 0.0282234106 |
| 66 | (909.7, 6.36) | 0.0282234106 |
| 67 | (747.4, 9.38) | 0.0287012166 |
| 68 | (832.9, 6.21) | 0.0289271134 |
| 69 | (155.1, 2.87) | 0.0289347031 |
| 70 | (977.7, 9.56) | 0.0298654782 |
| 71 | (610.9, 2.44) | 0.0303741714 |
| 72 | (235.1, 4.04) | 0.0303830303 |
| 73 | (685.1, 6.85) | 0.0303830303 |
| 74 | (670.4, 9.09) | 0.0307328580 |
| 75 | (346.1, 12.11) | 0.0308972074 |
| 76 | (217.2, 8.66) | 0.0309517132 |
| 77 | (770.9, 16.6) | 0.0310937661 |
| 78 | (163.2, 6.31) | 0.0313614024 |
| 79 | (392.3, 10) | 0.0317350792 |
| 80 | (469.7, 5.98) | 0.0317350792 |
| 81 | (470, 6.32) | 0.0317350792 |
| 82 | (794.9, 9.76) | 0.0317350792 |
| 83 | (357.3, 18.91) | 0.0318983292 |
| 84 | (303.7, 15.73) | 0.0325397156 |
| 85 | (221, 1.92) | 0.0328080364 |
| 86 | (999.5, 7.28) | 0.0330940901 |
| 87 | (637.3, 18.59) | 0.0335078063 |
| 88 | (331, 0.74) | 0.0336148466 |
| 89 | (978.8, 6.72) | 0.0338444022 |
| 90 | (271.1, 15.08) | 0.0347235687 |
| 91 | (801, 2.11) | 0.0348606916 |
| 92 | (599.5, 21.95) | 0.0358839090 |
| 93 | (769.4, 10.46) | 0.0371510791 |
| 94 | (914.1, 6.94) | 0.0375945952 |
| 95 | (363, 26.16) | 0.0381998666 |
| 96 | (235.1, 8.53) | 0.0382752828 |
| 97 | (273.2, 6.31) | 0.0390486612 |
| 98 | (250.1, 14.23) | 0.0401201887 |
| 99 | (585.2, 15.27) | 0.0406073368 |
| 100 | (276.2, 5.27) | 0.0414046782 |
| 101 | (183.1, 6.88) | 0.0419461253 |
| 102 | (430.3, 9.1) | 0.0421855472 |
| 103 | (229.2, 0.79) | 0.0424445226 |
| 104 | (811.6, 19.44) | 0.0438285232 |
| 105 | (126.2, 4.02) | 0.0439140255 |
| 106 | (708.5, 15.79) | 0.0439143789 |
| 107 | (127, 4.75) | 0.0442108301 |
| 108 | (338.2, 7.89) | 0.0444291108 |
| 109 | (391.3, 14.55) | 0.0444291108 |
| 110 | (714.6, 14.02) | 0.0444291108 |
| 111 | (665.3, 9.58) | 0.0446481623 |
| 112 | (875.7, 19.83) | 0.0446481623 |
| 113 | (676, 6.65) | 0.0447614386 |
| 114 | (695.1, 2.71) | 0.0448433123 |
| 115 | (480.2, 8.03) | 0.0451624233 |
| 116 | (754.6, 7.21) | 0.0454753333 |
| 117 | (494.9, 19.41) | 0.0454916992 |
| 118 | (785.1, 9.29) | 0.0455064285 |
| 119 | (265.2, 4.72) | 0.0456621220 |
| 120 | (771.9, 24.52) | 0.0460254955 |
| 121 | (467.2, 8.55) | 0.0464130076 |
| 122 | (869.9, 10.55) | 0.0464539626 |
| 123 | (479.3, 24.87) | 0.0473472790 |
| 124 | (380.3, 24.05) | 0.0475242732 |
| 125 | (194.1, 6.48) | 0.0475341652 |
| 126 | (262.6, 5.7) | 0.0475341652 |
| 127 | (694.2, 11.76) | 0.0475341652 |
| 128 | (695.9, 4.32) | 0.0475341652 |
| 129 | (660.8, 2.32) | 0.0475865516 |
| 130 | (958.8, 6.36) | 0.0482703924 |
| 131 | (504.3, 15.49) | 0.0484159645 |

TABLE 13 p-values for features differenced from baseline: time-48 hours samples

| ion number | m/z (Da), retention time (min) | p-value |
| --- | --- | --- |
| 1 | (715.8, 7.68) | 0.0005303918 |
| 2 | (919.5, 9.63) | 0.0012509535 |
| 3 | (802.4, 8.16) | 0.0016318638 |
| 4 | (922.5, 7.27) | 0.0023943584 |
| 5 | (741.5, 23.22) | 0.0038457139 |
| 6 | (875.4, 19.37) | 0.0044466656 |
| 7 | (878.9, 7.28) | 0.0052374088 |
| 8 | (996.1, 9.94) | 0.0060309508 |
| 9 | (295.9, 15.78) | 0.0070608315 |
| 10 | (521.4, 23.84) | 0.0075730074 |
| 11 | (676, 6.65) | 0.0075742521 |
| 12 | (703.9, 4.35) | 0.0075743621 |
| 13 | (716.2, 6.62) | 0.0078671775 |
| 14 | (346.1, 7.46) | 0.0080100576 |
| 15 | (551.4, 24.89) | 0.0086803932 |

TABLE 13-continued p-values for features differenced from baseline: time-48 hours samples

| ion number | m/z (Da), retention time (min) | p-value |
|---|---|---|
| 16 | (415.2, 9.09) | 0.0088869428 |
| 17 | (182.1, 2.44) | 0.0114906565 |
| 18 | (310.3, 19.13) | 0.0121106698 |
| 19 | (428.3, 6.2) | 0.0124220037 |
| 20 | (908.6, 10.83) | 0.0127529218 |
| 21 | (715.8, 4.37) | 0.0129735339 |
| 22 | (444.3, 2.8) | 0.0135088012 |
| 23 | (753.3, 9.34) | 0.0140485313 |
| 24 | (779.5, 19.79) | 0.0149169860 |
| 25 | (211.1, 13.48) | 0.0149614082 |
| 26 | (285.2, 19.8) | 0.0155513781 |
| 27 | (441.4, 19.09) | 0.0169697745 |
| 28 | (483.3, 6.17) | 0.0171647510 |
| 29 | (488.3, 6.38) | 0.0172240677 |
| 30 | (616.2, 11.9) | 0.0176526391 |
| 31 | (861.8, 9.74) | 0.0185440613 |
| 32 | (485.3, 23.17) | 0.0186867970 |
| 33 | (435.1, 4.14) | 0.0193706655 |
| 34 | (612.3, 16.87) | 0.0193706655 |
| 35 | (362.3, 5.65) | 0.0194196263 |
| 36 | (227, 23.11) | 0.0204130271 |
| 37 | (883.2, 9.76) | 0.0204386696 |
| 38 | (229.2, 0.79) | 0.0205101165 |
| 39 | (643.3, 5.67) | 0.0210117164 |
| 40 | (980.6, 7.44) | 0.0215182605 |
| 41 | (795.5, 20.72) | 0.0218437599 |
| 42 | (577.2, 3.56) | 0.0224776501 |
| 43 | (152.1, 1.51) | 0.0233549892 |
| 44 | (525.4, 15.11) | 0.0234730657 |
| 45 | (435.3, 19.92) | 0.0235646539 |
| 46 | (299.2, 25.54) | 0.0237259148 |
| 47 | (612.9, 0.36) | 0.0245420186 |
| 48 | (505.3, 12.78) | 0.0245629232 |
| 49 | (986.7, 7.42) | 0.0248142595 |
| 50 | (719.2, 6.07) | 0.0252229441 |
| 51 | (562.3, 19.13) | 0.0252471150 |
| 52 | (552.4, 22.8) | 0.0254361708 |
| 53 | (353.2, 19.3) | 0.0266840298 |
| 54 | (575.4, 16.74) | 0.0275127383 |
| 55 | (845.2, 6.33) | 0.0291304640 |
| 56 | (633.7, 6.14) | 0.0301224895 |
| 57 | (519.3, 13.32) | 0.0301986537 |
| 58 | (205.1, 13.28) | 0.0306513410 |
| 59 | (317.9, 1.41) | 0.0306513410 |
| 60 | (388.3, 9.86) | 0.0306513410 |
| 61 | (471.3, 26.3) | 0.0306513410 |
| 62 | (723.2, 6.69) | 0.0320817369 |
| 63 | (912.5, 10.13) | 0.0320817369 |
| 64 | (965.2, 2.77) | 0.0320817369 |
| 65 | (718.9, 5.76) | 0.0322905214 |
| 66 | (363, 26.16) | 0.0330856794 |
| 67 | (897.1, 9.53) | 0.0331382847 |
| 68 | (227.3, 6.92) | 0.0332507087 |
| 69 | (778.2, 14.75) | 0.0335555992 |
| 70 | (321, 2.35) | 0.0337995708 |
| 71 | (447.8, 6.29) | 0.0343295019 |
| 72 | (536.1, 4.09) | 0.0343295019 |
| 73 | (653.5, 19.99) | 0.0343565954 |
| 74 | (667.4, 21.32) | 0.0343565954 |
| 75 | (982.7, 9.73) | 0.0352875093 |
| 76 | (789.4, 6.11) | 0.0364395580 |
| 77 | (505.3, 18.48) | 0.0369258233 |
| 78 | (277, 0.2) | 0.0369277075 |
| 79 | (285.3, 12.09) | 0.0382728484 |
| 80 | (739.5, 18.01) | 0.0382728484 |
| 81 | (838.9, 0.39) | 0.0382728484 |
| 82 | (400.2, 5.79) | 0.0384511838 |
| 83 | (883.6, 7.04) | 0.0384732436 |
| 84 | (604.3, 19.85) | 0.0411740329 |
| 85 | (287.1, 4.72) | 0.0412206143 |
| 86 | (549.9, 4.23) | 0.0415068077 |
| 87 | (879.8, 4.42) | 0.0415426686 |
| 88 | (721.7, 20.36) | 0.0417134604 |
| 89 | (711.4, 16.81) | 0.0417360498 |
| 90 | (982.1, 9.39) | 0.0419790105 |
| 91 | (971.4, 10.51) | 0.0432043627 |
| 92 | (112.7, 1.05) | 0.0452851799 |
| 93 | (503.3, 14.33) | 0.0453240047 |
| 94 | (173.1, 23.44) | 0.0466828436 |
| 95 | (283.1, 4.96) | 0.0466865226 |
| 96 | (637.4, 6.78) | 0.0467959828 |
| 97 | (597.4, 15.92) | 0.0471002889 |
| 98 | (813.5, 9.83) | 0.0480402523 |
| 99 | (444.2, 6) | 0.0486844297 |
| 100 | (448.3, 9.24) | 0.0486916088 |
| 101 | (502.5, 4.01) | 0.0493775335 |
| 102 | (854.2, 5.79) | 0.0493775335 |

Example 2

Identification of Protein Biomarkers Using Quantitative Liquid Chromatography-Mass Spectrometry/Mass Spectrometry (LC-MS/MS)

2.1. Samples Received and Analyzed

As above, reference biomarker profiles were obtained from a first population representing 15 patients ("the SIRS group") and a second population representing 15 patients who developed SIRS and progressed to sepsis ("the sepsis group"). Blood was withdrawn from the patients at Day 1, time 0, and time 48 hours. In this case, 50-75 μL plasma samples from the patients were pooled into four batches: two batches of five and 10 individuals who were SIRS-positive and two batches of five and 10 individuals who were sepsis-positive. Six samples from each pooled batch were further analyzed.

2.2 Sample Preparation

Plasma samples first were immunodepleted to remove abundant proteins, specifically albumin, transferrin, haptoglobulin, anti-trypsin, IgG, and IgA, which together constitute approximately 85% (wt %) of protein in the samples. Immunodepletion was performed with a Multiple Affinity Removal System column (Agilent Technologies, Palo Alto, Calif.), which was used according to the manufacturer's instructions. At least 95% of the aforementioned six proteins were removed from the plasma samples using this system. For example, only about 0.1% of albumin remained in the depleted samples. Only an estimated 8% of proteins left in the samples represented remaining high abundance proteins, such as IgM and α-2 macroglobulin. Fractionated plasma samples were then denatured, reduced, alkylated and digested with trypsin using procedures well-known in the art. About 2 mg of digested proteins were obtained from each pooled sample.

2.3. Multidimensional LC/MS

The peptide mixture following trypsin digestion was then fractionated using LC columns and analyzed by an Agilent MSD/trap ESI-ion trap mass spectrometer configured in an LC/MS/MS arrangement. One mg of digested protein was applied at 10 μL/minute to a micro-flow $C_{18}$ reverse phase (RP1) column. The RP1 column was coupled in tandem to a Strong Cation Exchange (SCX) fractionation column, which in turn was coupled to a $C_{18}$ reverse phase trap column.

Figure 6:
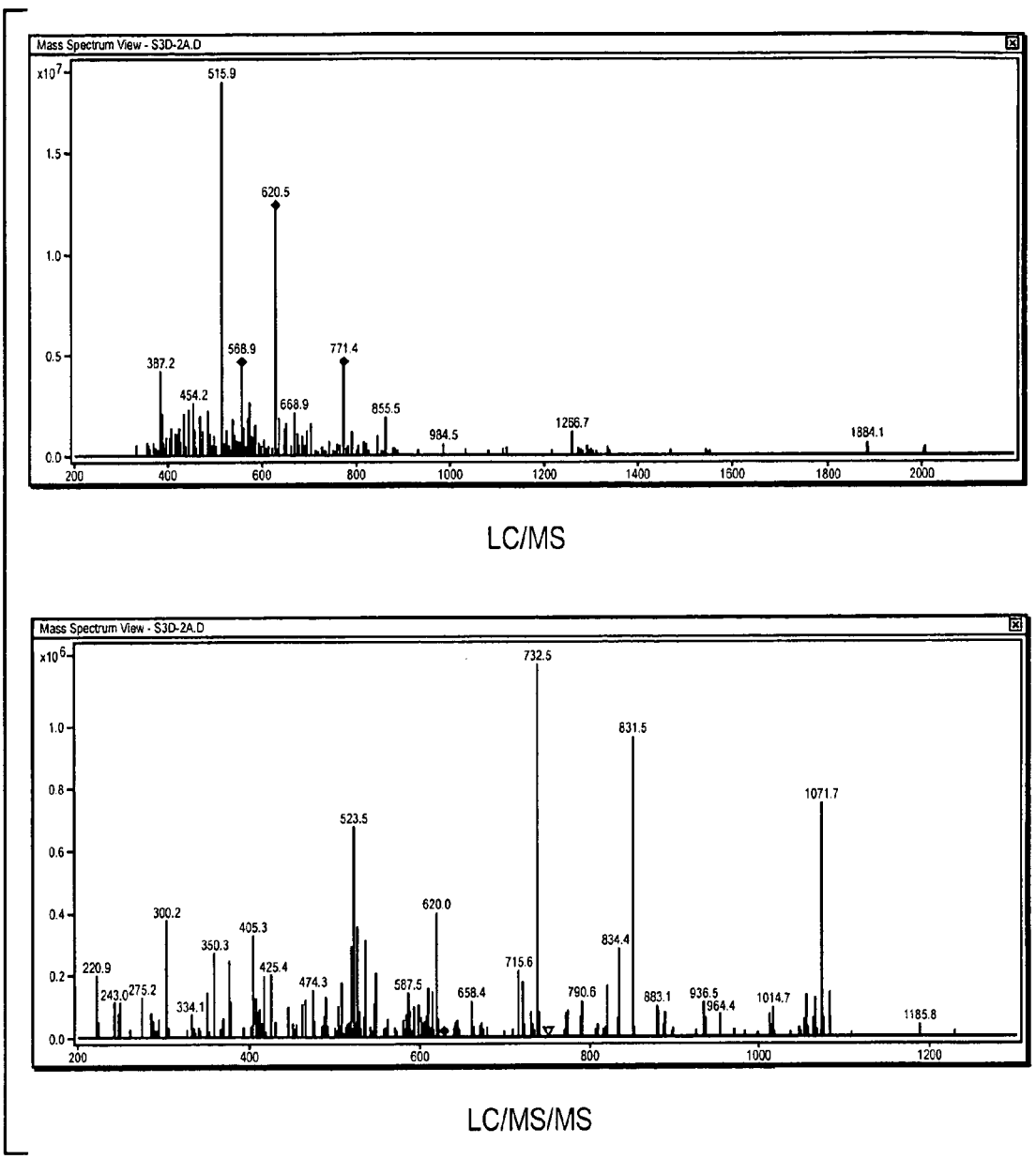
FIG. 6 shows representative LC/MS and LC/MS/MS spectra obtained on plasma samples, using the configuration described in the examples.

Samples were applied to the RP1 column in a first gradient of 0-10% ACN to fractionate the peptides on the RP1 column. The ACN gradient was followed by a 10 mM salt buffer elution, which further fractionated the peptides into a fraction bound to the SCX column and an eluted fraction that was immobilized in the trap column. The trap column was then removed from its operable connection with the SCX column and placed in operable connection with another $C_{18}$ reverse phase column (RP2). The fraction immobilized in the trap column was eluted from the trap column onto the RP2 column with a gradient of 0-10% ACN at 300 nL/minute. The RP2 column was operably linked to an Agilent MSD/trap ESI-ion trap mass spectrometer operating at a spray voltage of 1000-1500 V. This cycle (RP1-SCX-Trap-RP2) was then repeated to fractionate and separate the remaining peptides using a total ACN % range from 0-80% and a salt concentration up to 1M. Other suitable configurations for LC/MS/MS may be used to generate biomarker profiles that are useful for the invention. Mass spectra were generated in an t/z range of 200-2200 Da. Data dependent scan and dynamic exclusion were applied to achieve higher dynamic range. FIG. 6 shows representative biomarker profiles generated with LC/MS and LC/MS/MS.

2.4. Data Analysis and Results

For every sample that was analyzed in the MS/MS mode, about 150,000 spectra were obtained, equivalent to about 1.5 gigabytes of information. In total, some 50 gigabytes of information were collected. Spectra were analyzed using Spectrum Mill v 2.7 software (© Copyright 2003 Agilent Technologies, Inc.). The MS-Tag database searching algorithm (Millennium Pharmaceuticals) was used to match MS/MS spectra against a National Center for Biotechnology Information (NCBI) database of human non-redundant proteins. A cutoff score equivalent to 95% confidence was used to validate the matched peptides, which were then assembled to identify proteins present in the samples. Proteins that were detectable using the present method are present in plasma at a concentration of ~1 ng/mL, covering a dynamic range in plasma concentration of about six orders of magnitude.

A semi-quantitative estimate of the abundance of detected proteins in plasma was obtained by determining the number of mass spectra that were "positive" for the protein. To be positive, an ion feature has an intensity that is detectably higher than the noise at a given m/z value in a spectrum. In general, a protein expressed at higher levels in plasma will be detectable as a positive ion feature or set of ion features in more spectra. With this measure of protein concentration, it is apparent that various proteins are differentially expressed in the SIRS group versus the sepsis group: Various of the detected proteins that were "up-regulated" are shown in FIGS. 7A and 7B, where an up-regulated protein is expressed at a higher level in the sepsis group than in the SIRS group. It is clear from FIG. 7A that the level at which a protein is expressed over time may change, in the same manner as ion # 21 (437.2 Da, 1.42 min), shown in FIG. 4. For example, the proteins having GenBank Accession Numbers AAH15642 and NP_000286, which both are structurally similar to a serine (or cysteine) proteinase inhibitor, are expressed at progressively higher levels overtime in sepsis-positive populations, while they are expressed at relatively constant amounts in the SIRS—positive populations. The appearance of high levels of these proteins, and particularly a progressively higher expression of these proteins in an individual over time, is expected to be a predictor of the onset of sepsis. Various proteins that were down-regulated in sepsis-positive populations overtime are shown in FIGS. 8A and 8B. The expression of some of these proteins, like the unnamed protein having the sequence shown in GenBank Accession Number NP_079216, appears to increase progressively or stay at relatively high levels in SIRS patients, even while the expression decreases in sepsis patients. It is expected that these proteins will be biomarkers that are particularly useful for diagnosing SIRS, as well as predicting the onset of sepsis.

Having now fully described the invention with reference to certain representative embodiments and details, it will be apparent to one of ordinary skill in the art that changes and modifications can be made thereto without departing from the spirit or scope of the invention as set forth herein.

The invention claimed is:

1. A method of detecting the onset sepsis in a systemic inflammatory response syndrome ("SIRS")-positive individual using mass spectrometry, comprising:
    (a) obtaining a first biological sample taken from the SIRS-positive individual;
    (b) pre-treating the first biological sample, wherein said pre-treating comprises removing albumin, transferrin, haptoglobulin, anti-trypsin, IgG and IgA from the first biological sample, and
    (c) comparing (i) a first biomarker profile resolved from the pre-treated first biological sample using a mass spectrometry technique and (ii) a reference biomarker profile obtained from biological samples from a reference population; wherein a single such comparison classifies the individual as belonging to or not belonging to the reference population; wherein said individual's first biomarker profile and said reference biomarker profile comprise a plurality of ions each having a mass-to-charge ratio of about 200 Daltons to about 2200 Daltons; and wherein the comparison comprises applying a decision rule that detects the onset of sepsis in the SIRS-positive individual where the reference population is a SIRS-positive reference population confirmed as having sepsis after about 0-36 hours, a SIRS-positive reference population confirmed as having sepsis after about 36-60 hours, or a SIRS-positive reference population confirmed as having sepsis after about 60-84 hours.

2. The method of claim 1 wherein the reference population is a SIRS-positive reference population confirmed as having sepsis after about 0-36 hours.

3. The method claim 1, wherein the first biological sample is selected from the group consisting of blood and plasma.

4. The method of claim 1, wherein applying the decision rule comprises using a data analysis algorithm.

5. The method of claim 4, wherein the data analysis algorithm is a classification tree.

6. The method of claim 4, wherein the data analysis algorithm is nonparametric.

7. The method of claim 6, wherein the nonparametric algorithm is a Wilcoxon Signed Rank Test.

8. The method of claim 4, wherein the data analysis algorithm is a multiple additive regression tree.

9. The method of claim 4, wherein the data analysis algorithm is a logistic regression.

10. The method of claim 4, wherein the data analysis algorithm comprises at least two input parameters.

11. The method of claim 10, wherein the data analysis algorithm comprises at least five input parameters.

12. The method of claim 10, wherein the data analysis algorithm comprises at least ten input parameters.

13. The method of claim 10, wherein the data analysis algorithm comprises at least twenty input parameters.

14. The method of claim 1, wherein the decision rule determines the status of sepsis in with an accuracy of at least about 60%.

15. The method of claim 1, wherein the decision rule determines the status of sepsis with an accuracy of at least about 70%.

16. The method of claim 1, wherein the decision rule determines the status of sepsis with an accuracy of at least about 80%.

17. The method of claim 1, wherein the decision rule determines the status of sepsis with an accuracy of at least about 90%.

18. The method of claim 1, wherein the reference biomarker profile is obtained from a reference population comprising at least 20 individuals.

19. The method of claim 1, further comprising comparing a second biomarker profile from the SIRS-positive individual with a reference biomarker profile, wherein the second biomarker profile is obtained from a second biological sample taken from the SIRS-positive individual.

20. The method of claim 19, wherein the second biological sample from the SIRS-positive individual is taken about 24 hours after the first biological sample is taken from the SIRS-positive individual.

21. The method of claim 19, wherein the second biomarker profile is compared to a different reference biomarker profile than the first biomarker profile.

22. The method of claim 1, wherein said plurality of ions are detected by electrospray ionization mass spectrometry in positive mode.

23. The method of claim 1, wherein said mass spectrometry technique is selected from the group consisting of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorptionlionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCJ-MS/MS, APCI-(MS)$^n$, atmospheric pressure photoionization mass spectrometry (APPI-MS), APPI-MS/MS, and APPI-(MS)$^n$, quadrupole mass spectrometry, Fourier transform mass spectrometry (FTMS), and ion trap mass spectrometry, where n is an integer greater than zero.

24. The method of claim 1, wherein the reference population is a SIRS-positive reference population confirmed as having sepsis after about 36-60 hours.

25. The method of claim 1, wherein the reference population is a SIRS-positive reference population confirmed as having sepsis after about 60-84 hours.

* * * * *

UNITED STATES PATENT AND TRADEMARK OFFICE
CERTIFICATE OF CORRECTION

PATENT NO. : 7,645,613 B2  Page 1 of 1
APPLICATION NO. : 11/647688
DATED : January 12, 2010
INVENTOR(S) : Ivey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Sixteenth Day of November, 2010

David J. Kappos
*Director of the United States Patent and Trademark Office*